United States Patent
Vasan et al.

(10) Patent No.: US 11,998,178 B2
(45) Date of Patent: Jun. 4, 2024

(54) VIDEO LARYNGOSCOPE AND METHOD FOR USING SAME

(71) Applicant: Adroit Surgical, LLC, Oklahoma City, OK (US)

(72) Inventors: Nilesh R. Vasan, Oklahoma City, OK (US); Henry Paul Hagen, Gulf Shores, AL (US)

(73) Assignee: Adroit Surgical, LLC, Oklahoma City, OK (US)

( * ) Notice: Subject to any disclaimer, the term of this patent is extended or adjusted under 35 U.S.C. 154(b) by 342 days.

(21) Appl. No.: 17/458,874

(22) Filed: Aug. 27, 2021

(65) Prior Publication Data

US 2022/0061648 A1 Mar. 3, 2022

Related U.S. Application Data

(60) Provisional application No. 63/071,209, filed on Aug. 27, 2020.

(51) Int. Cl.
*A61B 1/267* (2006.01)
*A61B 1/00* (2006.01)
*A61B 1/06* (2006.01)

(52) U.S. Cl.
CPC ............ *A61B 1/267* (2013.01); *A61B 1/0005* (2013.01); *A61B 1/00096* (2013.01); *A61B 1/00165* (2013.01); *A61B 1/0684* (2013.01)

(58) Field of Classification Search
CPC ... A61B 1/267; A61B 1/0005; A61B 1/00096; A61B 1/00165; A61B 1/0684
USPC ......................................... 600/185, 188, 197
See application file for complete search history.

(56) References Cited

U.S. PATENT DOCUMENTS

| | | | | |
|---|---|---|---|---|
| 5,402,771 A | * | 4/1995 | Pilling | A61B 1/267 600/188 |
| 5,954,632 A | * | 9/1999 | Heckele | A61B 1/32 600/184 |
| 6,083,151 A | * | 7/2000 | Renner | A61B 1/042 600/188 |

(Continued)

FOREIGN PATENT DOCUMENTS

WO   WO 2019/197868 A1   10/2019

OTHER PUBLICATIONS

International Search Report and Written Opinion (PCT/US2021/048013), dated Mar. 14, 2022, 17 pages.

*Primary Examiner* — Eduardo C Robert
*Assistant Examiner* — David C Comstock
(74) *Attorney, Agent, or Firm* — DUNLAP CODDING, P.C.

(57) ABSTRACT

A laryngoscope is described. The laryngoscope has a handle, a tube, and a camera. The handle has proximal and distal ends. The tube has a proximal end, a distal end, a length extending between the proximal end and the distal end, and a first longitudinal axis along the length. The proximal end is connected to the proximal end of the handle. The tube has an inner surface defining a lumen internal space along the length. The lumen internal space creating a line of sight along a longitudinal axis through the tube. The camera is positioned on the inner surface of the tube to have a field of view out of the distal end of the tube. The camera has a second longitudinal axis offset from the first longitudinal axis of the tube, such that the line of sight along the first longitudinal axis through the tube is maintained.

14 Claims, 28 Drawing Sheets

(56) References Cited

U.S. PATENT DOCUMENTS

| | | | |
|---|---|---|---|
| 6,508,811 B2* | 1/2003 | Stihl | A61B 1/00105 600/196 |
| 9,386,915 B2* | 7/2016 | Vasan | A61B 1/0684 |
| 10,448,804 B2 | 10/2019 | McGrath et al. | |
| 2004/0210114 A1* | 10/2004 | Simon | A61M 16/0484 600/185 |
| 2012/0259176 A1* | 10/2012 | Grey | A61B 1/267 600/188 |
| 2014/0107422 A1* | 4/2014 | Huels | A61B 1/00105 600/188 |
| 2014/0316206 A1 | 10/2014 | Vasan | |
| 2015/0173598 A1* | 6/2015 | Alexander | A61B 1/015 600/187 |
| 2016/0183766 A1* | 6/2016 | Tsai | A61B 1/00105 600/188 |
| 2016/0250432 A1* | 9/2016 | Hendrix | A61B 1/00177 600/188 |
| 2019/0059710 A1* | 2/2019 | Molnar | A61B 1/2676 |

* cited by examiner

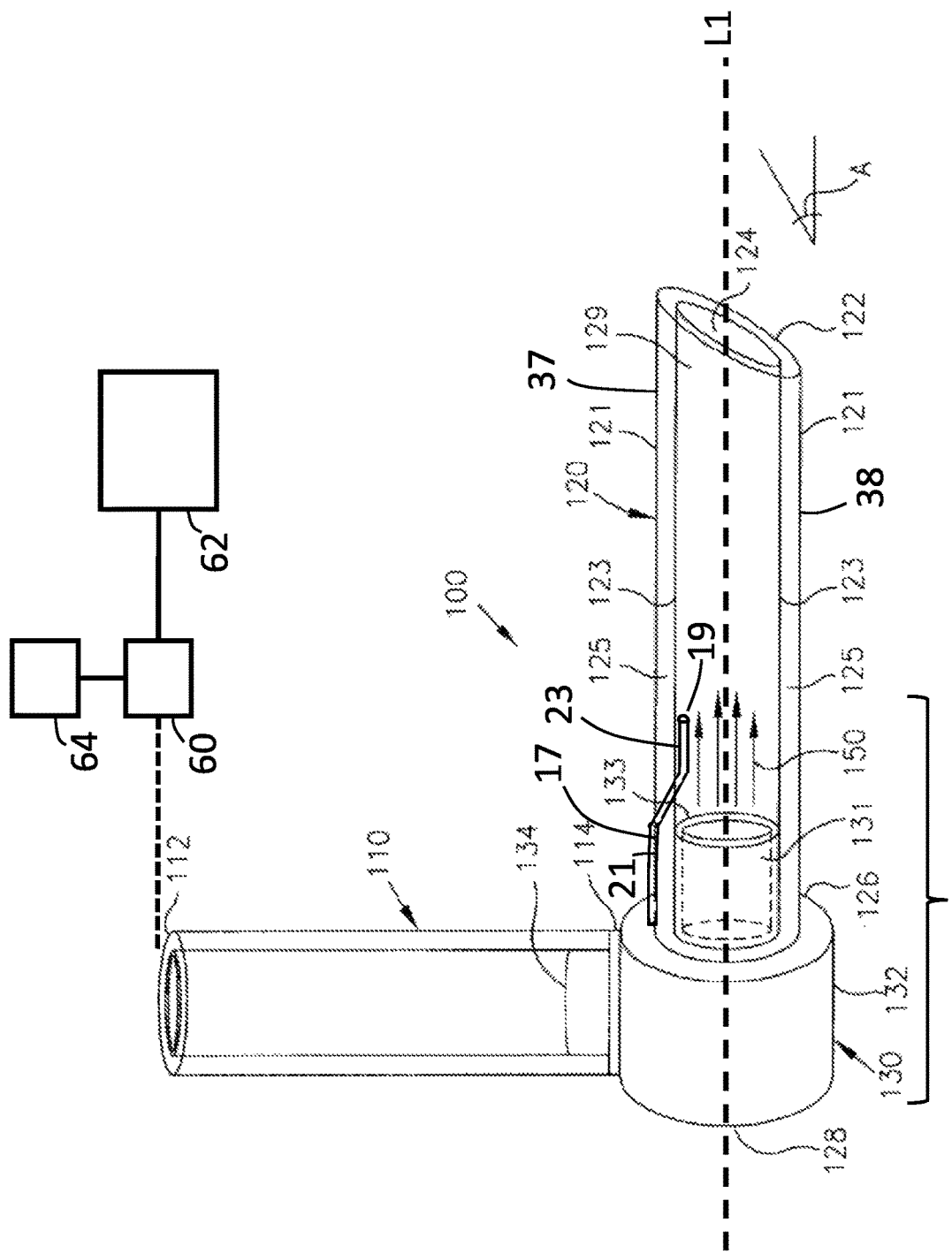

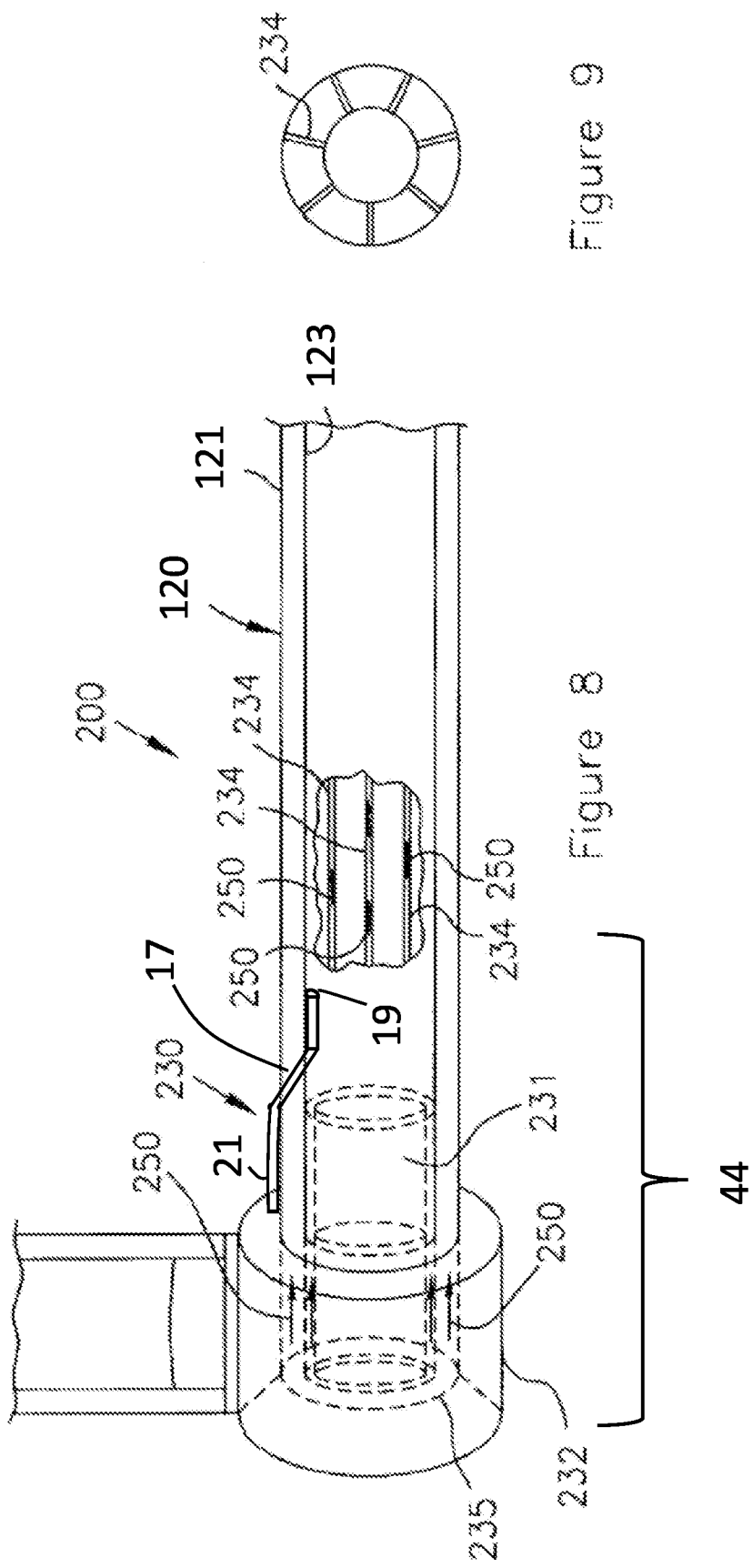

VIDEO LARYNGOSCOPE AND METHOD FOR USING SAME

CROSS REFERENCE TO RELATED APPLICATIONS/INCORPORATION BY REFERENCE STATEMENT

This application is a non-provisional application claiming benefit to the U.S. Provisional Application Ser. No. 63/071,209 entitled "VIDEO LARYNGOSCOPE AND METHOD FOR USING SAME" filed on Aug. 27, 2020, the entire contents of which are hereby incorporated herein by reference.

FIELD OF THE DISCLOSURE

The disclosure generally relates to laryngoscopes and methods of use of laryngoscopes. More particularly the disclosure relates to laryngoscopes having capabilities for image transmission, such as to a video monitor via cable and/or wirelessly, and capture, such as video capture.

BACKGROUND

A laryngoscope is used to assist with the placement of an endotracheal tube and/or a tracheal introducer such as a "bougie" into a patient's airway to provide oxygen to the patient, such as to connect to Bag Valve mask or a ventilator. Prior laryngoscopes used either a straight or curved blade to move the tongue, jaw, and/or epiglottis of a patient to allow a view of the patient's vocal cords, which are used for locating the patient's larynx and, subsequently, the trachea for insertion of the tube into the airway (and/or insertion of a bougie to guide insertion of the tube). This reduces the risk of intubating the patient's esophagus, which would cause air to be blown into the stomach, causing stomach distension and vomiting, as well as depriving the patient of oxygen, and possibly causing death.

The presence of blood, saliva, and vomit secretions can interfere with the proper placement of the laryngoscope. Further, in emergency situations, the proper placement of the laryngoscope must be done in a quick and safe manner.

Additionally, some prior laryngoscopes included a camera and monitor for viewing the interior of the patient's throat. However, these cameras were located at the leading insertion end of the laryngoscope. This placement causes the camera lens to fog up when it is inserted into the warmth of the throat. Additionally, the placement of the camera on a blade of the prior laryngoscopes makes it prone to be occluded by even a drop of blood, vomit, or other fluids. Prior art camera laryngoscopes required the use of a monitor for all situations, which were subject to glare, but were the only view of the throat once inserted since these cameras typically interfere with and occlude a user's direct view of the interior of the patient's throat. Further, the bulky size of prior laryngoscopes made them difficult to use in the field or in emergency situations outside of a hospital setting.

Therefore, there is a need for an improved video laryngoscope that can be used in difficult or emergency situations in and out of a medical facility that provides healthcare providers with a better view of the patient's larynx and is easier to use.

SUMMARY

Video laryngoscopes, video laryngoscope systems, and video laryngoscope methods of use are disclosed. The problem of bulky, hard-to-use, and ineffective prior video laryngoscopes is addressed through video laryngoscopes configured for ease of use in the field or in hospital situations.

In one implementation, a laryngoscope may comprise a handle having a proximal end and a distal end; a tube having a proximal end, a distal end, a length extending between the proximal end and the distal end, and a first longitudinal axis along the length of the tube, the proximal end connected to the proximal end of the handle, the tube having an inner surface defining a lumen internal space along the length of the tube, the lumen internal space creating a line of sight along the first longitudinal axis through the tube; and a camera positioned on the inner surface of the tube to have a field of view out of the distal end of the tube, the camera having a second longitudinal axis offset from the first longitudinal axis of the tube, such that the line of sight along the first longitudinal axis through the tube is maintained.

A method of use of a laryngoscope, may comprise inserting a tube of a laryngoscope into a mouth of a patient, the tube having a proximal end, a distal end, a length extending between the proximal end and the distal end, and a central longitudinal axis along the length of the tube, the tube having an inner surface defining a lumen internal space along the length of the tube, the lumen internal space creating a line of sight along a longitudinal axis through the tube, the proximal end of the tube connected to a proximal end of a handle; and obtaining video images of from a camera positioned on the inner surface of the tube and having a field of view out of the distal end of the tube, the camera having a longitudinal axis offset from the longitudinal axis of the tube, such that the line of sight along the longitudinal axis through the tube is maintained.

A laryngoscope may comprise a handle having a proximal end and a distal end; a tube having a proximal end, a distal end, a length extending between the proximal end and the distal end, and a first longitudinal axis along the length of the tube, the proximal end connected to the proximal end of the handle, the tube having an inner surface defining a lumen internal space along the length of the tube and an outer surface, the lumen internal space creating a line of sight along the first longitudinal axis through the tube; and a camera positioned on the outer surface of the tube to have a field of view beyond the distal end of the tube, the camera having a second longitudinal axis offset from the first longitudinal axis of the tube, such that the line of sight along the first longitudinal axis through the tube is maintained.

A camera system attachment device for attachment to a laryngoscope, may comprise a camera support having a rigid member with a longitudinal axis and an opening along the longitudinal axis, the camera support having a proximal end and a distal end, the camera support configured to be positioned within a lumen of a laryngoscope; a camera assembly positioned within the opening, the camera assembly comprising a camera positioned toward the distal end of the camera support; and a connector attached to the camera support and connectable to a handle of the laryngoscope to secure the camera support in the lumen of the laryngoscope.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale, or in schematic in the interest of clarity and conciseness. Not every component may be labeled in every drawing. Like reference numerals in the figures may represent and refer to the same or similar element or function. In the drawings:

FIG. 5 is a perspective view of another exemplary video laryngoscope in accordance with the present disclosure.

FIG. 8 is a partial perspective view of another exemplary video laryngoscope in accordance with the present disclosure.

FIG. 9 is a rear view of components of the video laryngoscope of FIG. 8.

DETAILED DESCRIPTION

Figure 1:
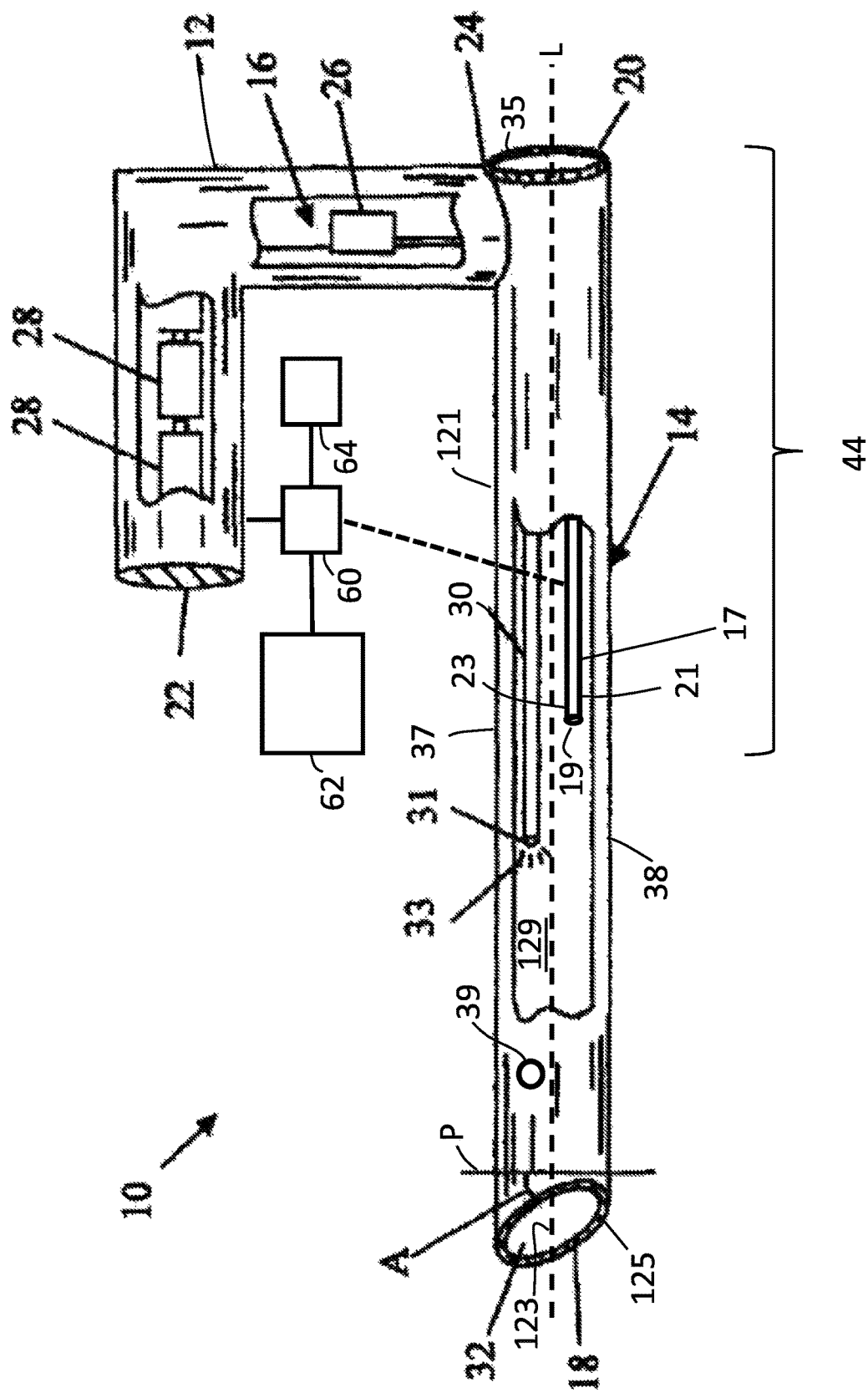
FIG. 1 is a partial-cut-away side view of an exemplary video laryngoscope in accordance with the present disclosure.

The following detailed description refers to the accompanying drawings. The same reference numbers in different drawings may identify the same or similar elements.

The mechanisms proposed in this disclosure circumvent the problems described above. The present disclosure describes video laryngoscopes, video laryngoscope systems, and video laryngoscope methods of use.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

The use of the term "at least one" or "one or more" will be understood to include one as well as any quantity more than one. In addition, the use of the phrase "at least one of X, V, and Z" will be understood to include X alone, V alone, and Z alone, as well as any combination of X, V, and Z. The use of the term "one or more Xs" will be understood to include X alone, as well as more than one X.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Further, the phrase "based on" is intended to mean "based, at least in part, on" unless explicitly stated otherwise.

As discussed above, typical laryngoscopes do not have video capability, do not combine video capability with direct manual visibility, and/or are too large and cumbersome for ease of use and transport. The present disclosure addresses these deficiencies with video laryngoscopes and methods of use.

Referring now to the drawings, FIG. 1 illustrates an exemplary video laryngoscope 10 in accordance with the present disclosure. The video laryngoscope 10 may comprise a handle 12, a tube 14, and a camera assembly 17 connected to the cylindrical tube 14. The video laryngoscope 10 may further comprise an optical subassembly 16, which may be contained within and extending between the handle 12 and the tube 14.

Figure 2:
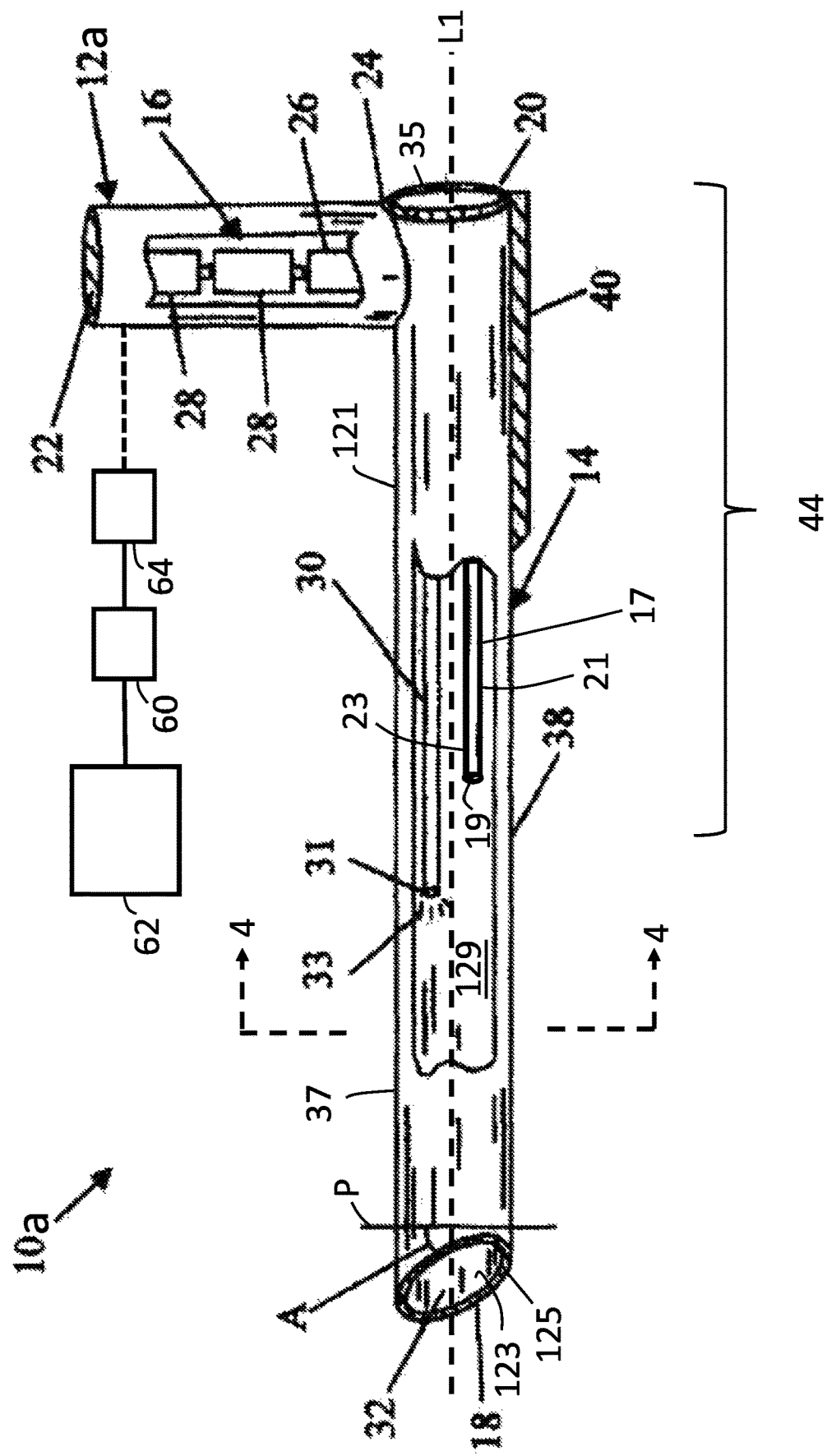
FIG. 2 is a partial-cut-away side view of another exemplary video laryngoscope in accordance with the present disclosure.
Figure 3:
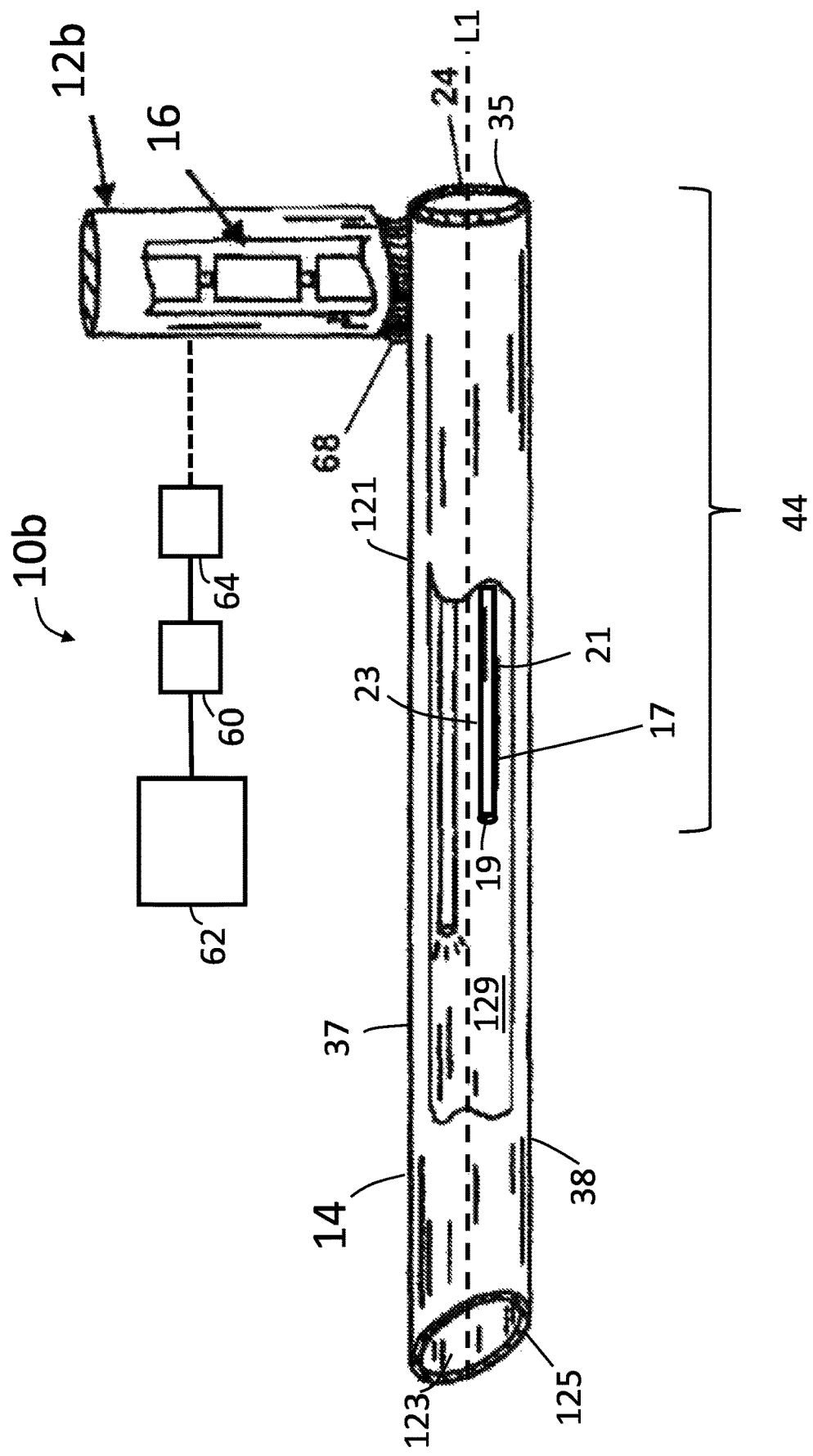
FIG. 3 is a partial-cut-away side view of another exemplary video laryngoscope in accordance with the present disclosure.

The handle 12 has a distal end 22 and a proximal end 24. In some implementations, the handle 12 of the video laryngoscope 10 may have a bent configuration as illustrated in FIG. 1. In other implementations, another exemplary video laryngoscope 10a, as shown in FIG. 2, may have a handle 12a having a straight configuration. In other implementations, another exemplary video laryngoscope 10b, as shown in FIG. 3, comprises a handle 12b hingedly connected to the tube 14, such as by a hinge 68. The handle 12, 12a, 12b may be detachable from the tube 14. In some implementations, the handle may be connectable to the tube 14 with a rotatable laryngoscope connector (for example, one that meets the ISO 7376 standard). However, it will be understood that the hinge 68 and connector are merely illustrative and not limiting. Those schooled in the art would recognize other forms of moveable connections or fixed connections can be utilized with the present disclosure. Additionally, in some implementations, the tube 14 may be connected to prior art laryngoscope handles.

The video laryngoscopes 10a, 10b are substantially similar to the video laryngoscope 10, except as shown and described. Implementations describing the use of the video laryngoscope 10 apply equally to the video laryngoscopes 10a, 10b, except where described.

As shown in FIGS. 1-3, the tube 14 has a distal end 18 having a distal end opening 32 and a proximal end 20 having a proximal end opening 35, and a length extending between the distal end 18 and the proximal end 20. The distal end opening 32 may be oriented at an angle (A) relative to a latitudinal cross-sectional plane (P) of the tube 14. The angle (A) of the distal end opening 32 may aid in the insertion of the tube 14 into the mouth and throat of a patient. In some implementations, the tube 14 may have a top 37 orientated toward the handle 12 and may have a bottom 38 opposite the top 37. The angle (A) of the distal end opening 32 may be orientated such that the top 37 has a first length and the bottom 38 has a second length shorter than the first length.

The tube 14 is hollow, which allows the operator to view inside the mouth and throat of a patient. The tube 14 has an outer surface 121 and an inner surface 123 with a thickness 125 therebetween, which may be referred to as the wall 125 of the tube 14. The inner surface 123 defines an open passage, known as the lumen 129, which extends the length of the tube 14. The lumen 129 has a central longitudinal axis (L1) extending the length of the tube 14 in the approximal center of the tube 14. In some implementations, the central longitudinal axis (L1) may be substantially perpendicular to the handle 12, 12a, 12b. In some implementations, the handle 12, 12a, 12b may be positioned at an acute or obtuse angle in relation to the central longitudinal axis (L1). In some implementations, the plane (P) may be substantially perpendicular to the central longitudinal axis (L1).

The shape of the tube 14 may be cylindrical or other geometries besides or in addition to cylindrical. The tube 14 may be of various uniform and non-uniform roundness, including oblong, and may have non-uniform radius size from the proximal end 20 to the distal end 18, and further may be oblong at one end and circular at the other. In some implementations, the distal end 18 has a first diameter and the proximal end 20 has a second diameter smaller than the first diameter. In some implementations, the distal end 18 is oblong and has a first size and the proximal end 20 is circular and has a second size smaller than the first size. The lumen 129 has a minimum diameter which may be defined by the smallest cross-section of the interior of the tube 14 along the length of the tube 14.

The proximal end 20 of the tube 14 may be connected or connectable to the proximal end 24 of the handle 12. The connection of the tube 14 and the handle 12 may be of a unitary construction or of separate construction.

The tube 14 may be substantially rigid. The tube 14 may be made from a suitable plastic, metal, transparent material, translucent material, or combination thereof. The use of partially or completely transparent and/or translucent material may aid with the illumination of the tube 14 along its length. This is useful in situations where blood or other items can hinder the ability to view the interior of the mouth and/or throat of the patient. The video laryngoscope 10 may be of different lengths and widths.

Figure 4:
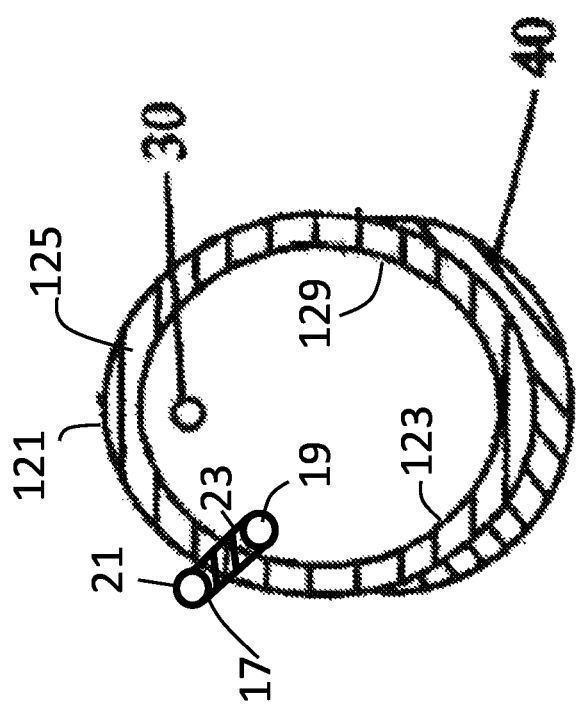
FIG. 4 is a cross-sectional view of a portion of the exemplary video laryngoscope of FIG. 2 in accordance with the present disclosure.
Figure 5A:
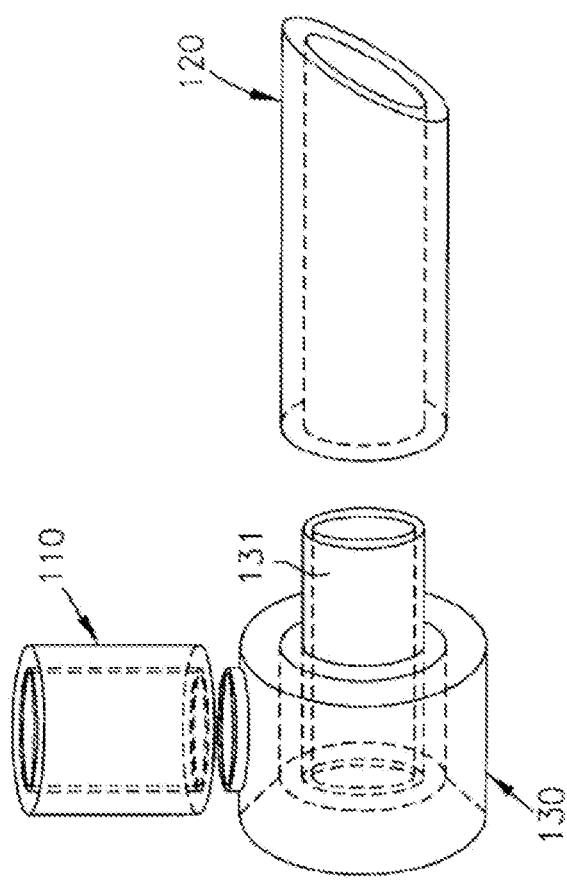
FIG. 5A is an exploded perspective view of components of the video laryngoscope of FIG. 5.

In some implementations, the video laryngoscope 10 may comprise a protective portion 40, as illustrated in FIGS. 2 and 4. The protective portion 40 may include a strip of protective material located along the outer surface 121 of the tube 14 near the proximal end 20 of the tube 14. The protective portion 40 may be rubber, silicon, or other suitable flexible and/or cushioning material. In use, the protective portion 40 may be utilized to protect the teeth and soft tissue of the patient.

In some implementations, as illustrated in FIG. 1, the tube 14 may have one or more side ports 39. In use, the side ports 39 may be utilized for suction and/or jet ventilation.

The optical subassembly 16 comprises a light source 26 and a power source 28. The light source 26 may be partially or completely located within the handle 12 and/or the tube 14. The light source 26 may be partially or completely located on the exterior of the handle 12 and/or on the outer surface 121 of the tube 14. The light source 26 may be one or more solid state light, such as one or more light emitting diode.

The power source 28 may be partially or completely located within the handle 12, and is in communication with the light source 26. The power source 28 may include one or more batteries. In some implementations, the power source 28 may be external to the handle 12. In some implementations, the power source 28 may connected to the light source 26 through a cable. In some implementations, the power source 28 may include a wall socket, a computer, a computing device, or other device having or connected to an external power source.

In some implementations, the optical subassembly 16 may further comprise a light carrier 30 in communication with the light source 26, extending into the cylindrical tube 14, and configured to transmit light 33 from the light source 26. The light carrier 30 may include fiber optic cables or other similar devices. The light carrier 30 may terminate within the cylindrical tube 14. The light carrier 30 may have a distal end 31 that terminates between the proximal end 20 and the distal end 18 of the cylindrical tube 14 and emits the light 33. The light 33 may illuminate the interior of the tube 14, travel out the distal end opening 32 of the tube 14, and/or travel through the wall 125 of the tube 14. In use, the light 33 may illuminate the mouth and throat of a patient, thereby aiding a user in placing the video laryngoscope 10 within the mouth and throat of the patient.

The camera assembly 17 may comprise a camera 19. The camera 19 may comprise a fiber optic camera 19 and/or a cable with a lens (such as a chip-tip camera) or other types of image capturing sensor(s). For simplicity, the camera 19 may be referred to herein as a fiber optic camera 19. The camera 19 may be positioned on and/or within the wall 125 of the tube 14. In some implementations, at least a lumen portion 23 of the camera 19 may be positioned in the lumen 129 of the tube 14. In some implementations, the camera 19 may be positioned on the outside of the tube 14. The camera 19 may be positioned such that it does not obstruct a line-of-sight through the lumen 129 of the tube 14. In some implementations, the camera 19 may be positioned anywhere along the length of the lumen 129 of the tube. In some implementations, the camera 19 may be positioned closer to the proximal end 20 than the distal end 18 of the tube 14. The camera 19 may be focused to have a field of view beyond the distal end 18 of the tube 14, and/or have an adjustable focal length.

The camera 19 may be configured to capture one or more images of an area beyond the distal end 18 of the tube 14, such as structures in the throat of the patient, when the video laryngoscope 10 is in use. The camera 19 may be configured to convert received light into electrical signals indicative of one or more images, which may be in the form of video, i.e., a series of moving visual images.

In some implementations, the camera assembly 17 may comprise one or more fiber optic cable 21 connected to, or part of, the camera 19. The fiber optic cable 21 may be positioned through the wall 125 of the tube 14 and/or the fiber optic cable 21 may be positioned through the tube 14 into the handle 12. In some implementations, the fiber optic cable 21 may be connected through the handle 12 to the one or more display 62 and/or the one or more computer processors 60. In some implementations, the camera assembly 17 may comprise a plug which is connectable to an external fiber optic cable for connection to the one or more display 62 and/or the one or more computer processors 60.

The moving images of the video may be displayed on one or more display screens 62, such as a computer monitor, a handheld computer tablet screen, a smartphone screen, a large screen for group viewing and/or instruction, a table top display, a handheld display, and/or a screen on other user devices. In some implementations, one or more of the display screen(s) 62 is part of and/or physically connected to the video laryngoscope 10. For example, in some implementations, the display screen may be attached to the handle 12. In some implementations, one or more of the display screen(s) 62 are separate from the other components of the video laryngoscope 10.

The images on the display screen 62 may be magnified and/or displayed at a size larger than the size of the structure(s) depicted in the image to assist the user in placing the tube 14 of the video laryngoscope 10 into the patient's trachea.

In some implementations, the images may be transmitted wirelessly to the display screen(s) 62 and/or the computer processor(s) 60, and/or may be transmitted via one or more physical connection, such as fiber optic cable or other cable. In some implementations, wireless transfer of the images to the display screen 62 may be in accordance with Bluetooth standards, such as those promulgated by the Bluetooth Special Interest Group. In some implementations, wireless transfer may be accomplished through WiFi technology and standards, such as those promulgated by IEEE. In some implementations, wireless transfer may be accomplished through mirroring technology. In some implementations, the camera assembly 17 may comprise one or more "chip-on-tip" device in which the camera 19 comprises an imaging sensor, and the imaging sensor is connected to the fiber optic cable 21. In some implementations, the imaging sensor may be one or more charge-coupled device and/or complementary metal-oxide semiconductor. The camera 19 may further comprise one or more lens.

In some implementations, the camera assembly 17 may comprise two or more cameras 19. The two or more cameras 19 may be positioned to provide depth perception and/or multi-dimensional capacity.

In some implementations, a lumen portion 23 of the camera assembly 17, including the camera 19, is positioned within the lumen 129 of the tube 14. The lumen portion 23 of the camera assembly 17 may be positioned on and/or connected to the inner surface 123 of the wall 125 of the tube 14. The lumen portion 23 of the camera assembly 17 may be positioned along the length of the tube 14. In some implementations, the lumen portion 23 of the camera assembly 17 may be positioned closer to the proximal end 20 than the distal end 18 of the tube 14. In some implementations, the camera 17 and/or the lumen portion 23 of the camera assembly may be positioned in the tube 14 at the junction of the handle 12 and the tube 14.

The lumen portion 23 of the camera assembly 17 has a longitudinal axis L2. In some implementations, the lumen portion 23 of the camera assembly 17 has a maximum diameter that is less than the minimum diameter of the lumen 129 of the tube 14. The maximum diameter of the camera assembly 17 may be approximately 10% or less than the minimum diameter of the lumen 129 of the tube 14. The maximum diameter of the camera assembly 17 may be configured such that the line of sight of the operator through the lumen 129 along the central longitudinal axis of the lumen 129 is not interrupted or is minimally interrupted. In some implementations, the camera 19 may have a diameter of approximately 0.25 mm to approximately 10 mm. In some implementations, the camera 19 may have a diameter of approximately 3 mm. The longitudinal axis L2 of the lumen portion 23 of the camera assembly 17 may be parallel to and offset from the central longitudinal axis L1 of the lumen 129 of the tube 14.

In some implementations, the camera assembly 17 is combined with the optical subassembly 16. In some implementations, one or more components of the camera assembly 17 are combined with one or more components of the optical subassembly 16. For example, in some implementations, the camera assembly 17 and the optical subassembly 16 may share one or more power source 28.

In some implementations, the camera assembly 17 and/or the optical subassembly 16 may be sealed and waterproof.

In some implementations, as shown in FIG. 1, the fiber optic cable 21 may connect the fiber optic camera 19 to one or more computer processor 60, such that the electrical signals may be transferred from the fiber optic camera 19 to the one or more computer processor 60. The one or more computer processors 60 may be implemented as a single or plurality of computer processors 60 working together, or independently to execute software code to carry out methods as described herein. Exemplary embodiments of the one or more computer processors 60 include a digital signal processor (DSP), a central processing unit (CPU), a field programmable gate array (FPGA), a microprocessor, a multi-core processor, a printed circuit board (PCB), and/or combinations thereof. The one or more computer processors 60 may be capable of communicating with one or more non-transitory computer readable memory 64.

It is to be understood that in certain embodiments using more than one computer processor 60, the one or more computer processors 60 may be located remotely from one another, located in the same location, or comprising a unitary multi-core processor (not shown). The one or more computer processors 60 may be capable of reading and/or executing the computer executable code and/or of retrieving, creating, manipulating, altering, and/or storing computer data structures into the one or more non-transitory computer readable memory 64, such as into the one or more databases. The computer executable code may comprise program logic. The computer executable code when executed by the one or more computer processor 60, may cause the one or more computer processor 60 to carry out one or more actions.

Additionally, the one or more non-transitory computer readable memory 64 may be implemented as a conventional non-transitory memory, such as, for example, random access memory (RAM), a hard drive, a solid-state drive, a flash drive, a memory card, a non-transitory optical drive, and/or combinations thereof. It is to be understood that while one or more non-transitory computer readable memory 64 may be located in the same physical location as the one or more computer processors 60 and/or one or more the display screens 62, the one or more non-transitory computer readable memory 64 may be located remotely from the one or more computer processors 60, and may communicate with the one or more computer processors 60 via a network. Additionally, when more than one non-transitory computer readable memory 64 is used, a first memory may be located in the same physical location as the one or more computer processors 60 and/or one or more display screens 62, and additional memories may be located in a remote physical location from the one or more computer processors 60. The physical location(s) of the one or more non-transitory computer readable memory 64 may be varied. Additionally, one or more non-transitory computer readable memory 64 may be implemented as a "cloud memory" (i.e., one or more non-transitory computer readable memory 64 may be partially or completely based on or accessed using a network).

In some implementations, one or more of the computer processor(s) and/or the non-transitory computer readable memory 64 may be located within the handle 12. In some implementations, one or more of the computer processor(s) 60 and/or the non-transitory computer readable memory 64 may be located separately from the tube 14 or the handle 12 of the video laryngoscope 10.

Another exemplary video laryngoscope 100 is illustrated in FIGS. 5-13. The video laryngoscope 100 is substantially similar to the video laryngoscope 10, 10a, 10b, except as described below. The video laryngoscope 100 may comprise a handle assembly 110, a tube 120, and the camera assembly 17. The video laryngoscope 100 may further comprise an optical subassembly 130 extending between the handle assembly 110 and the tube 120. The tube 120, the handle assembly 110, the optical subassembly 130, and/or the camera assembly 17 may be a unitary construction or of separate construction as shown in FIG. 5A. Further, the cylindrical tube 120, the handle assembly 110, the optical subassembly 130, and/or the camera assembly 17 may be constructed partially or completely of one or more disposable materials and/or may be coated in one or more disposable materials.

As shown in FIG. 5, the handle assembly 110 has a distal end 112 and a proximal end 114 which is connected to the optical subassembly 130. The proximal end 114 may be removably secured to the optical subassembly 130.

The tube 120 has a distal end 122 and a proximal end 126, and a length extending between the distal end 122 and the proximal end 126. The proximal end 126 may be connected to the optical subassembly 130. The proximal end 126 may be removably secured to the optical subassembly 130. The proximal end 126 of the tube 120 may be fixedly, removably, and/or hingedly connected to the proximal end 114 of the handle assembly 110.

The tube 120 has an outer surface 121 and an inner surface 123 with a thickness 125 therebetween, which may be referred to as the wall 125 of the tube 120. The inner surface 123 defines an open passage, known as the lumen 129, which extends the length of the tube 120. The distal end 122 of tube 120 has a distal end opening 124 providing access to the lumen 129. The lumen 129 has a central longitudinal axis (L1) extending the length of the tube 14 in the approximal center of the tube 14.

The proximal end 126 has a proximal end opening 128 providing access to the lumen 129. The distal end opening 124 may be oriented at an angle (A) relative to a ninety-degree cross-sectional plane of tube 120. The angle (A) of the distal end opening 124 may aid in the insertion of the tube 120 into the mouth and trachea of a patient.

The shape of the tube 120 may be cylindrical or other geometries besides or in addition to cylindrical. The tube 120 may be of various uniform and non-uniform roundness, including oblong, and may have non-uniform radius size from the proximal end 126 to the distal end 122 and further may be oblong at one end and circular at the other. In some implementations, the distal end 122 has a first diameter and the proximal end 126 has a second diameter smaller than the first diameter. In some implementations, the distal end 18 is oblong and has a first size and the proximal end 20 is circular and has a second size smaller than the first size.

The tube 120 may be constructed of a translucent material. However, one skilled in the art will understand the material from which the tube 120 is made can include other types of materials, including non-translucent material and transparent material. The use of partially or completely transparent and/or translucent material may aid with the illumination of the tube 120 along its length. This is useful in situations where blood or other items can hinder the ability to view the interior of the mouth and/or throat of the patient. The video laryngoscope 100 may be of different lengths and widths.

Figure 6:
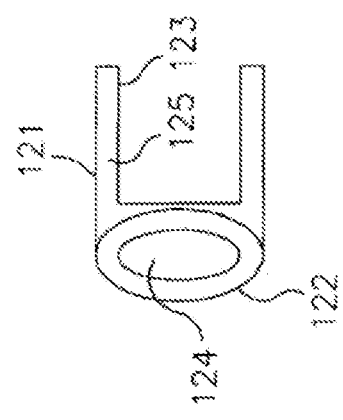
FIG. 6 is a front perspective view of components of the video laryngoscope of FIG. 5.
Figure 7:
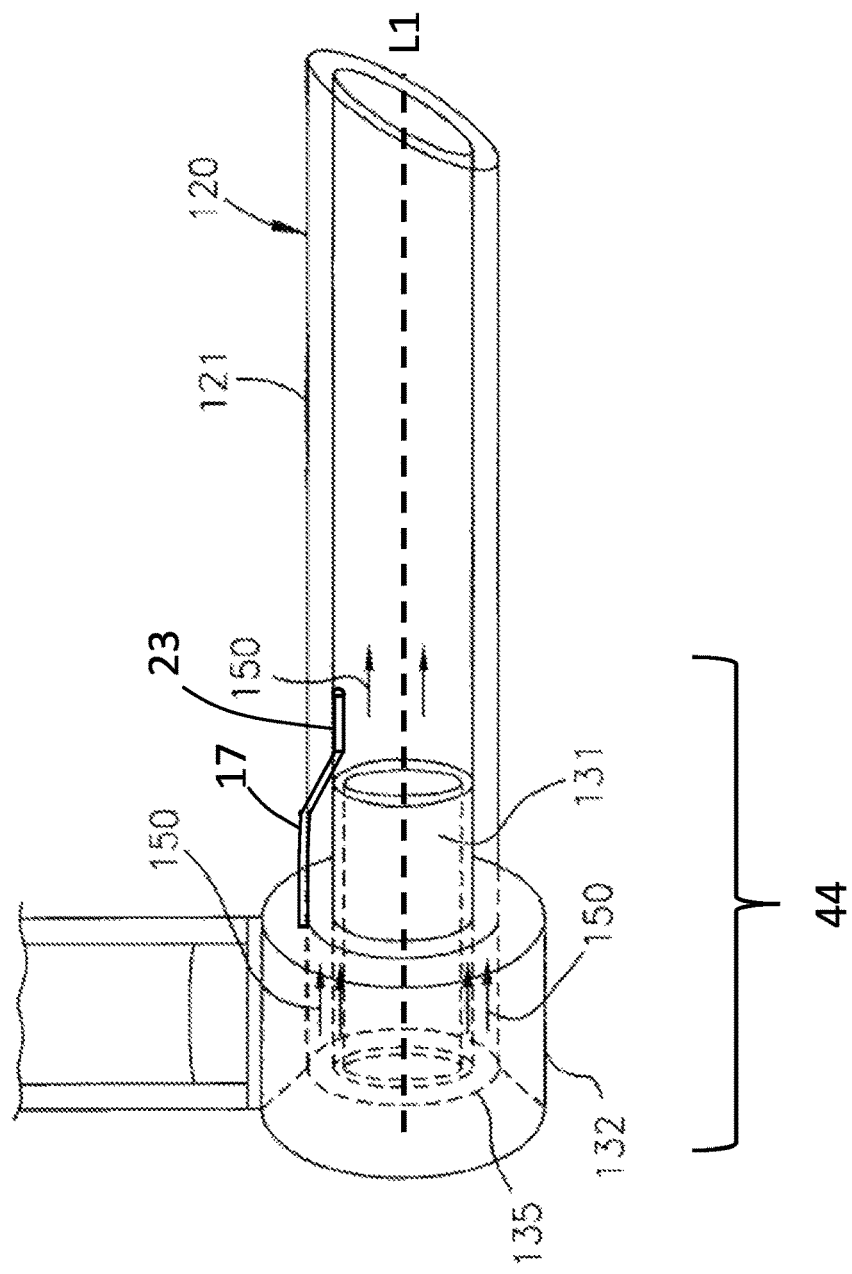
FIG. 7 is a perspective view of components of an exemplary video laryngoscope in accordance with the present disclosure.

As shown in the FIGS. 5-7, the optical subassembly 130 may have a light source housing 132, and may be removably secured to the tube 120 such that the outer surface of the optical subassembly 130 is continuous with the outer surface 121. The optical subassembly 130 may have an opening 131 that extends the length of the optical subassembly 130 and that corresponds to the lumen 129. In some implementations, the optical subassembly 130 and the lumen 129 may both be centered around the central longitudinal axis L1 of the lumen 129. In some implementations, the optical subassembly 130 may have a longitudinal axis parallel to the longitudinal axis L1 of the lumen 129.

In use, the opening 131 may allow for the proper placement of the tube 120 in a patient. The operator may look into the opening 131 and through optical subassembly 130 and proximal end opening 128 and look through lumen 129 and through to distal end opening 124 to see inside the mouth and throat of a patient, when the video laryngoscope 100 is inserted into the patient.

The optical subassembly 130 may comprise a light source 135 configured to provide light 150. In some implementations, the light source 135 may provide light 150 such that the light 150 is transmitted in the lumen 129 of the tube 120 from the proximal end 126 through the distal end 122. The light source 135 may be positioned within the light source housing 132. This light may aid the operator in visualizing the larynx despite obstructions such as blood and vomit.

In some implementations, a power source 134 may be located within the handle assembly 110 and may be connected to the light source 135 and/or the camera assembly 17. In some implementations, the power source 134 may be located externally from the handle assembly 110 and may be connected to the light source 135 and/or the camera assembly 17.

Figure 7A:
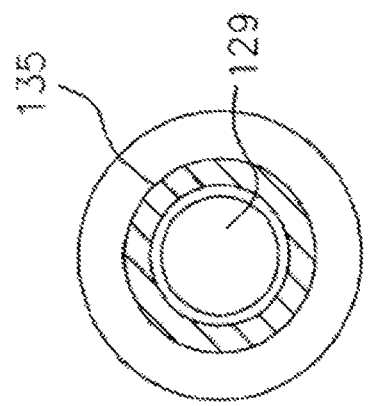
FIG. 7A is a rear view of components of the video laryngoscope of FIG. 7.

As shown in FIGS. 7 and 7A, the light source 135 may be circular. However, other shapes may also be utilized. The light source 135 can be any light source that can project sufficient light into and through the tube 120, including one or more solid illuminating lights and/or one or more light emitting diodes. In some implementations, the light source 135 may be a ring of light emitting diodes.

As shown in FIG. 5, in some implementations, the optical subassembly 130 may have an inner portion 133. The inner portion 133 may direct the light 150 into the lumen 129 and thereby illuminate the interior of the tube 120 and through the tube 120, such as out of the distal end 122 of the tube 120.

In some implementations, the light source 135 may project the light 150 through the wall 125 of tube 120. In doing so, the light 150 may illuminate the outer surface 121 and/or the inner surface 123 of the tube 120, thereby transferring the light 150 out of the tube 120.

In some implementations, the outer surface 121 of the wall 125 of the tube 120 may be partially or completely covered with a light-blocking coating, such that the light 150 is not transmitted beyond the outer surface 121 of the wall 125 along the length of the tube 120, but rather exits the lumen 129 through the distal end opening 124 and/or through the distal end 122. The light 150 may still be transmitted through the inner surface 123 and within the wall 125, and within the lumen 129, along the length of the tube 120 to exit out through the distal end opening 124 and/or through the distal end 122. In some implementations, the outer surface 121 of the wall 125 of the tube may be partially or completely constructed of an opaque material, such that the light 150 is not transmitted beyond the outer surface 121 of the wall 125 (or portions of the wall 125 made of the opaque material) along the length of the tube 120, but rather exits the lumen 129 through the distal end opening 124.

In some implementations, the light source 135 may illuminate the exterior of the tube 120 along with the lumen 129 of the tube 120. For example, when the tube 120 is constructed of translucent and/or transparent material, the translucent and/or transparent material may transfer the light 150 through the wall 125 as well as through the lumen 129.

In some implementations, the light source 135 may be located around the circumference of the tube 120 at or near its proximal end 126. The light 150 from the light source 135 may travel along the length of tube 120, illuminating the outer surface 121 and/or the inner surface 123 of the tube 120. The light may be transferred through the wall 125 along the length of the tube 120. The light 150 may illuminate the circumference of the lumen 129 of the tube 120. In use, the light 150 may aid the operator in visualizing the larynx despite obstructions such as blood and vomit.

Figure 12:
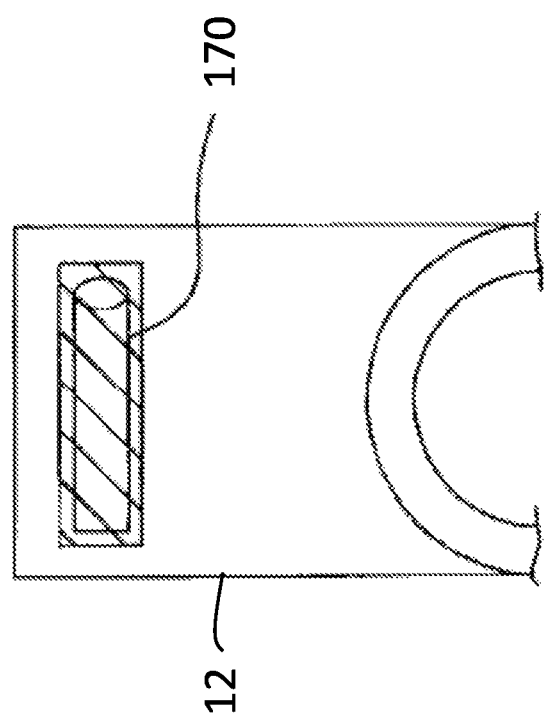
FIG. 12 is a partial perspective view of an exemplary video laryngoscope in accordance with the present disclosure.

As shown in FIG. 12, in some implementations, the optical subassembly 130 may comprise a toggle switch 170 connected to and configured to activate and deactivate the light source 135. The toggle switch 170 may be positioned on the handle 12, for example. The toggle switch 170 may be configured to dim or increase the amount of the light 150 provided by the light source 135. Nonexclusive examples of the toggle switch 170 include a button, slide switch, pull strip, and external signals. In a disposable implementation, the toggle switch 170 may be a pull strip that engages circuitry to provide power to the light source 135, such that once activated the power will not be disengaged until the power source 134 is drained. 310

FIGS. 8 and 9 illustrate another exemplary video laryngoscope 200, similar to the video laryngoscopes 10, 10a, 10b, 100, except as described. The video laryngoscope 200 includes an optical subassembly 230 comprising a light source housing 232 having a light source 235 located therein. The light source 235 may project light 250 through and within the wall 125 of the tube 120 between the outer surface 121 and the inner surface 123. A plurality of light channels 234 are located around the circumference of, and extend the length of, the tube 120. The light channels 234 may extend from the outer surface 121 to the inner surface 123. The light 250 from the light source 235 may be projected into the plurality of light channels 234. The light 250 may then illuminate the outer surface 121 and/or inner surface 123.

Figure 10:
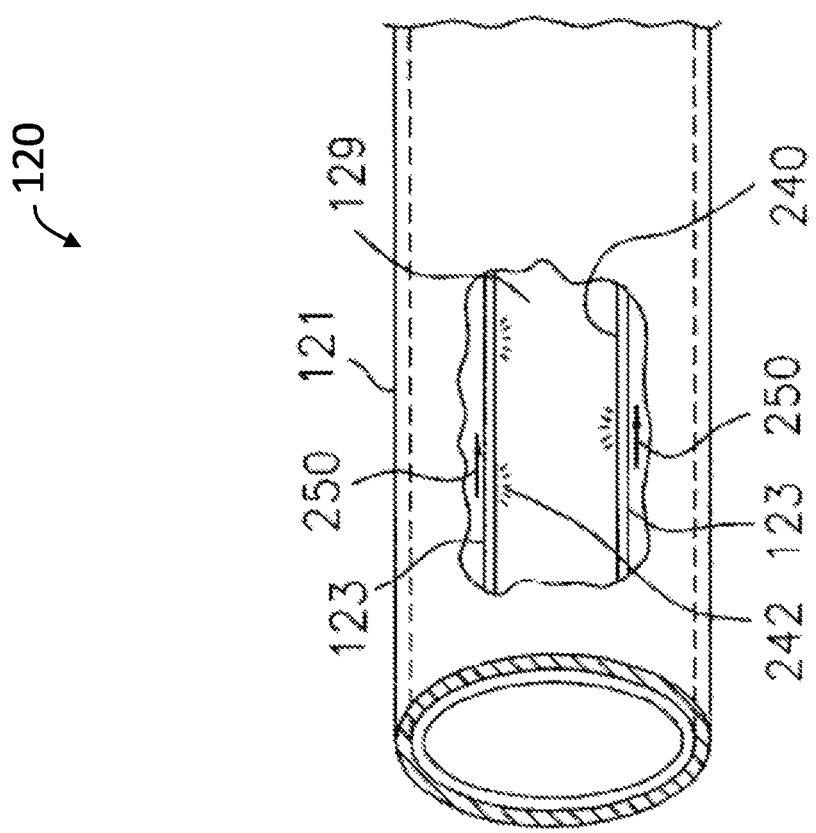
FIG. 10 is a partial cut-away perspective view of an exemplary video laryngoscope in accordance with the present disclosure.

In some implementations, as shown in FIG. 10, the inner surface 123 of the tube 120 may be coated with an opaque material 240 to reduce glare from the light being projected therein. When the opaque material 240 is used with the tube 120, openings 242 within opaque material 240 may be positioned around the circumference and length of the inner surface 123. The openings 242 allow for the light 250 to penetrate into the lumen 129 of the tube 120. The coating can also act to avoid glare into the operator's eye.

Figure 11:
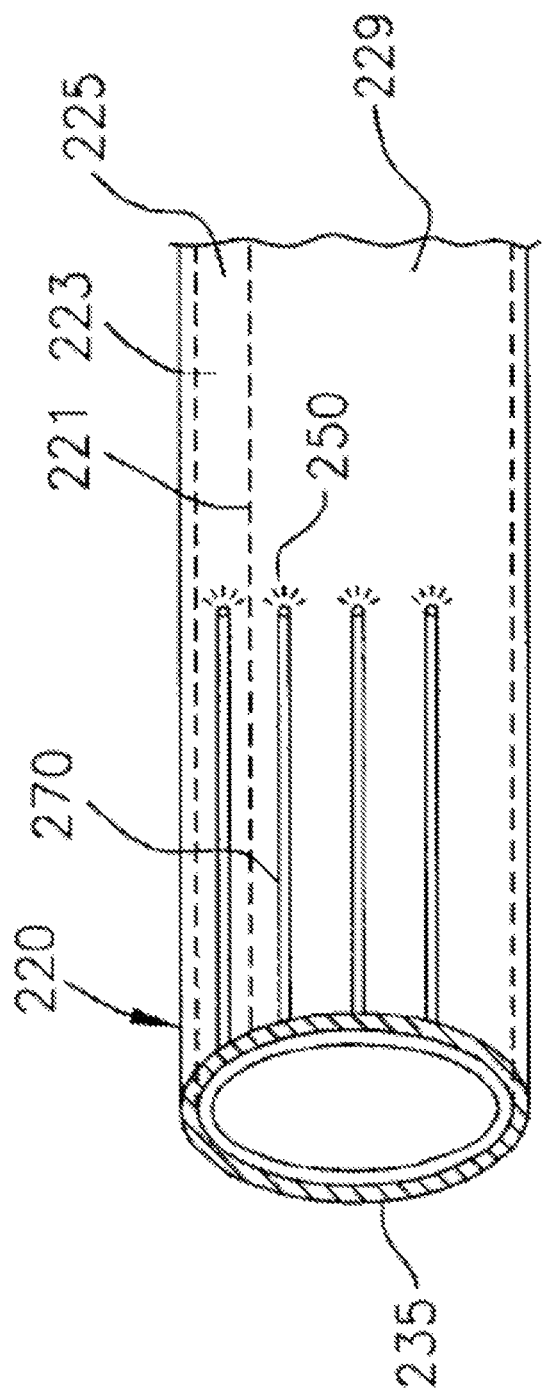
FIG. 11 is a partial perspective view of an exemplary video laryngoscope in accordance with the present disclosure.

In some implementations, as shown in FIG. 11, one or more fiber optic lines 270 may extend from the light source 235 and through the wall 125 of the cylindrical tube 120 between the outer surface 121 and the inner surface 123. The fiber optic lines 270 may be configured to transfer the light 250 to illuminate the outer surface 121 and/or inner surface 123, along with the lumen 229 along the length of the cylindrical tube 220.

Figure 13:
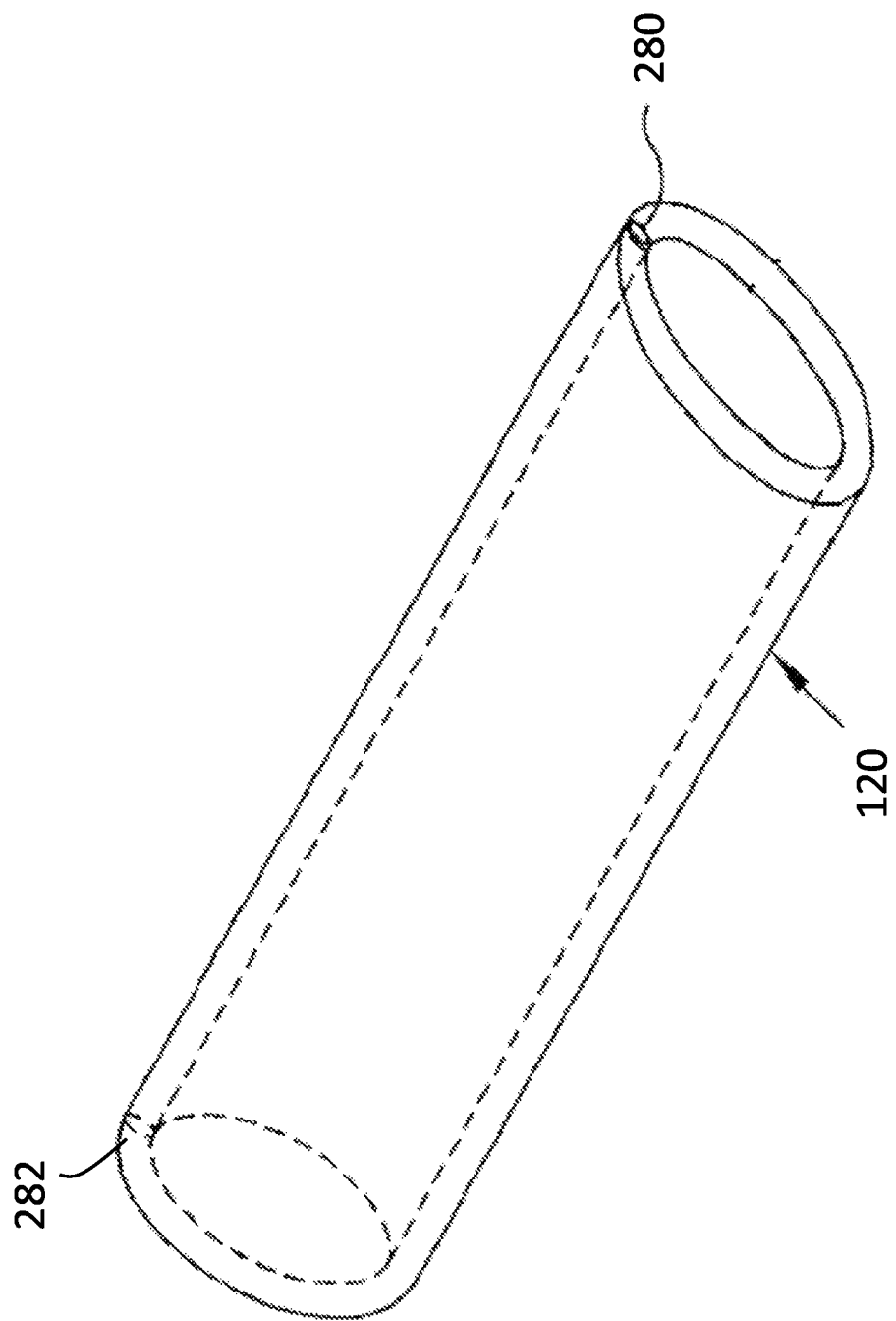
FIG. 13 is a partial perspective view of components of an exemplary video laryngoscope in accordance with the present disclosure.

In some implementations, as shown in FIG. 13, the cylindrical tube 120 may have a side tube 280. The side tube 280 may have an elongation such that it can pass between the vocal cords into the trachea for use as a "ventilating bronchoscope". The side tube 280 may be secured to the cylindrical tube 120 and/or the handle 12. In some implementations, the side tube 280 may be located within the lumen 129 of the cylindrical tube 120. In some implementations, the side tube 280 may be located within the wall 125. The side tube 280 may have an opening 282 at the proximal end 20 of the cylindrical tube 120 which may be located on the outside of cylindrical tube 120 to accommodate instruments, attachments, and/or other tools. In use, the side tube 280 may allow ventilation of the patient using general anesthesia equipment, for example.

Figure 14:
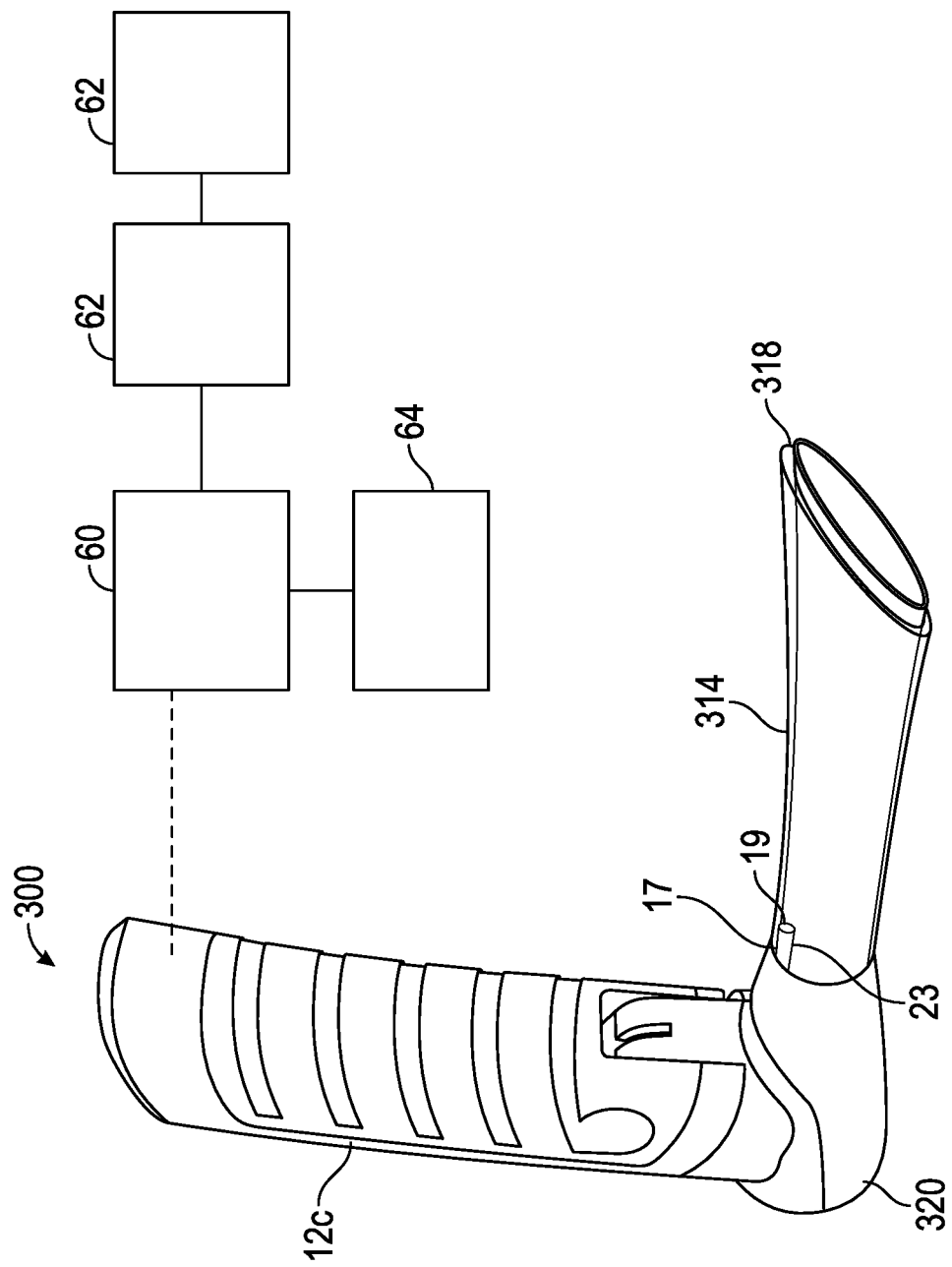
FIG. 14 is a schematic view of an exemplary video laryngoscope system in accordance with the present disclosure.
Figure 15:
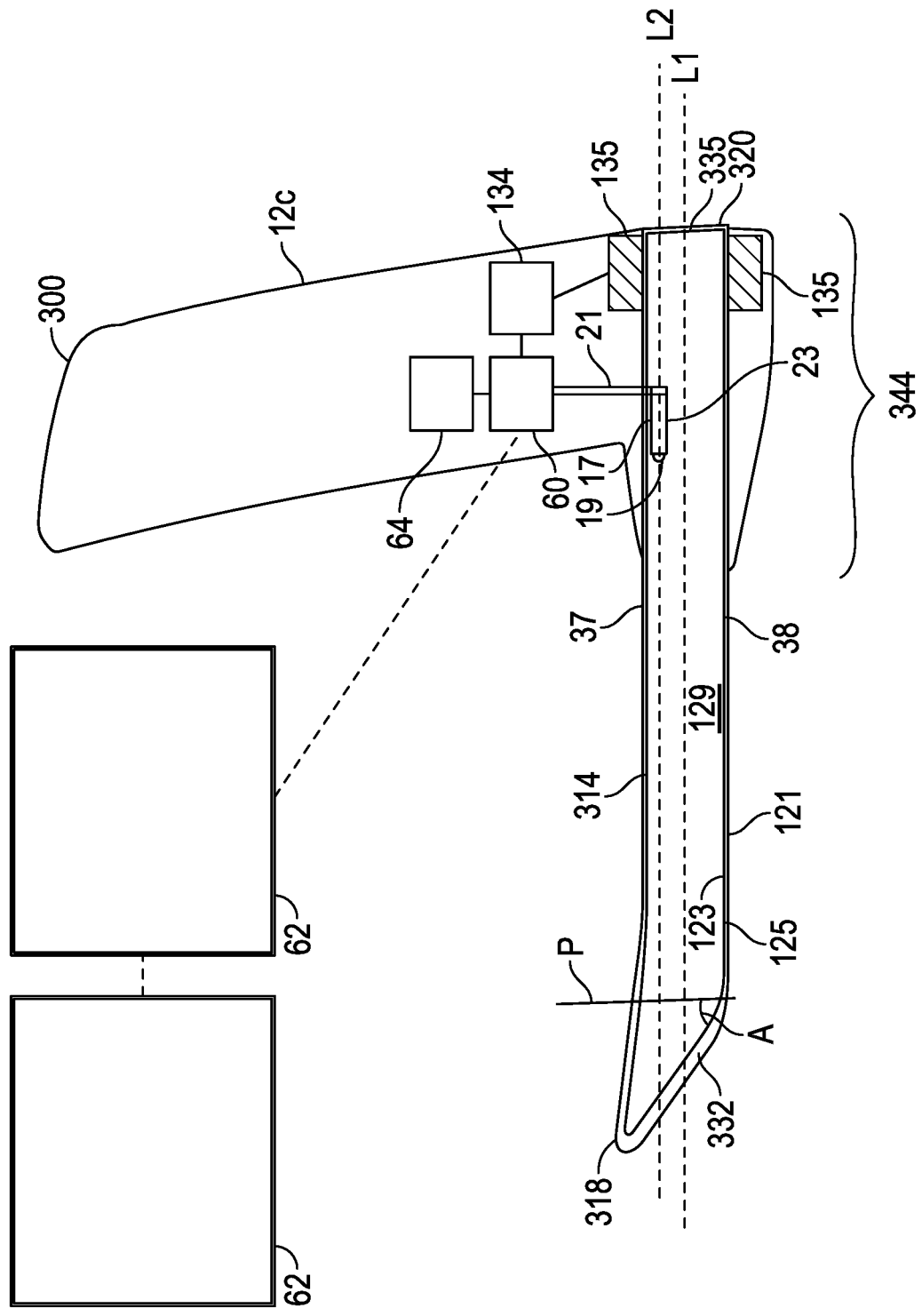
FIG. 15 is a cross-sectional view of the video laryngoscope of FIG. 14.
Figure 16:
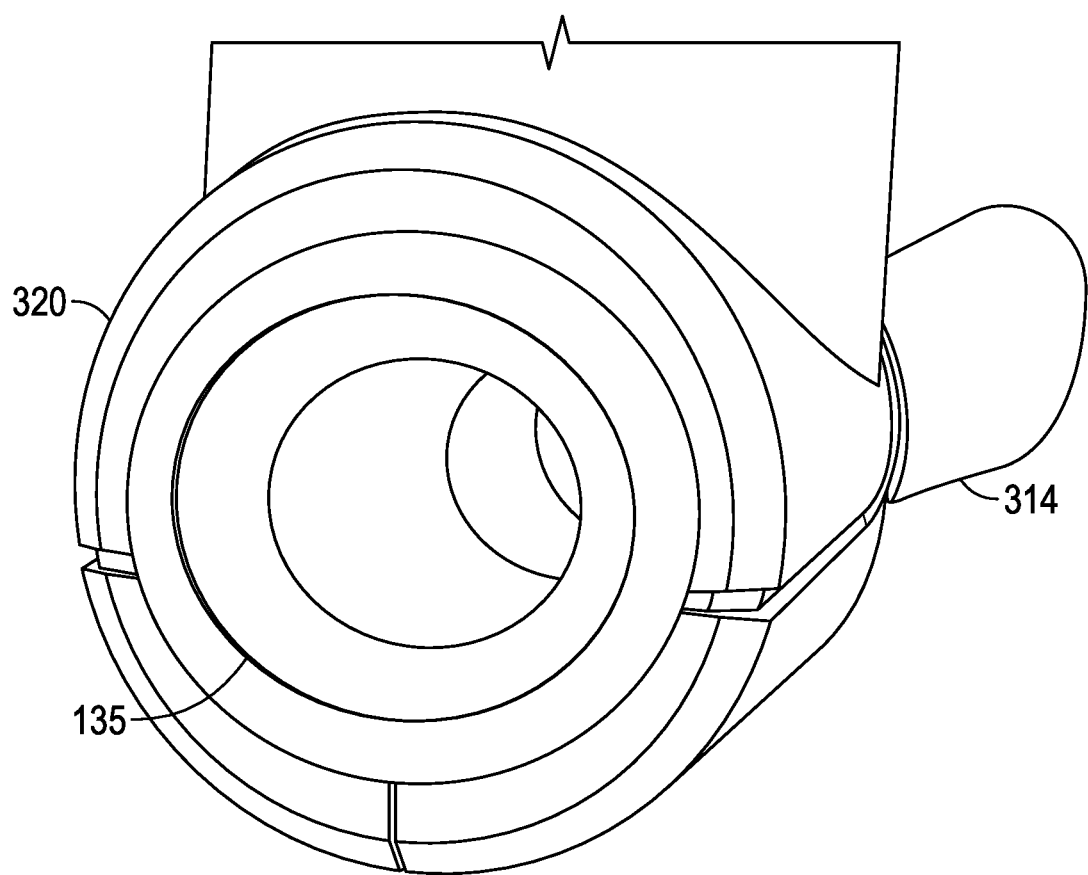
FIG. 16 is a partial rear view of the video laryngoscope of FIG. 14.

FIGS. 14-16 illustrate another exemplary video laryngoscope 300 that is substantially similar to the video laryngoscopes 10, 10a, 10b, 100, except as shown and described. The video laryngoscope 300 may comprise a handle 12c, a tube 314, and the camera assembly 17 connected to the tube 314. The video laryngoscope 10 may further comprise the light source 135. As previously described, the light source 135 may be one or more solid illuminating lights and/or one or more light emitting diodes. In some implementations, the light source 135 may be circular. In some implementations, the light source 135 may be a ring of light emitting diodes positioned on the outer surface 321 of the tube 314.

The tube 314 has a distal end 318 having a distal end opening 332 and a proximal end 320 having a proximal end opening 335, and a length extending between the distal end 318 and the proximal end 320. The distal end opening 332 may be oriented at an angle (A) relative to a latitudinal cross-sectional plane (P) of the tube 314. The tube 314 is hollow, which allows the operator to view inside the mouth and throat of a patient. The tube 314 has an outer surface 321 and an inner surface 123 with a thickness 125 therebetween, which may be referred to as the wall 125 of the tube 314. The inner surface 123 defines an open passage, known as the lumen 129, which extends the length of the tube 314. The lumen 129 has a central longitudinal axis (L1) extending the length of the tube 314 in the approximal center of the tube 314.

The shape of the tube 314 may be cylindrical or other geometries besides or in addition to cylindrical. The tube 314 may be of various uniform and non-uniform roundness, including oblong, and may have non-uniform radius size from the proximal end 320 to the distal end 318, and further may be oblong at one end and circular at the other. In some implementations, the distal end 318 has a first diameter and the proximal end 320 has a second diameter smaller than the first diameter. In some implementations, the distal end 318 is oblong and has a first size and the proximal end 320 is circular and has a second size smaller than the first size. The lumen 129 has a minimum diameter which may be defined by the smallest cross-section of the interior of the tube 314 along the length of the tube 314. In some implementations, a portion or all of the tube 314 may have a flat bottom, such that the tube 314 has a partial-circular cross section.

The proximal end 320 of the tube 314 may be connected or connectable to the proximal end 324 of the handle 12c. The connection of the tube 314 and the handle 12c may be of a unitary construction or of separate construction. The connection may be hinged, or otherwise moveable.

The tube 314 may be substantially rigid. The tube 314 may be made from a suitable plastic, metal, transparent material, translucent material, or combination thereof. The use of transparent and/or translucent material may aid with the illumination of the tube 314 along its length. The video laryngoscope 10 may be of different lengths and widths.

The longitudinal axis L2 of the lumen portion 23 of the camera assembly 17 may be parallel to and offset from the central longitudinal axis L1 of the lumen 129 of the tube 314. In some implementations, the lumen portion 23 of the camera assembly 17 has a maximum diameter that is less than the minimum diameter of the lumen 129 of the tube 314. The maximum diameter of the camera assembly 17 may be approximately 10% or less than the minimum diameter of the lumen 129 of the tube 314. The maximum diameter of the camera assembly 17 may be configured such that the line of sight of the operator through the lumen 129 along the central longitudinal axis of the lumen 129 is not interrupted or is minimally interrupted. In some implementations, the camera 19 may have a diameter of approximately 0.25 mm to approximately 10 mm.

In some implementations, the lumen portion 23, including the camera 19, is located within the lumen 129. In some implementations, the lumen portion 23, including the camera 19, is positioned near to, or in contact with the inner surface 123. In some implementations, the lumen portion 23, including the camera, is located outside of the tube 314, such as on the outer surface 121.

Figure 17:
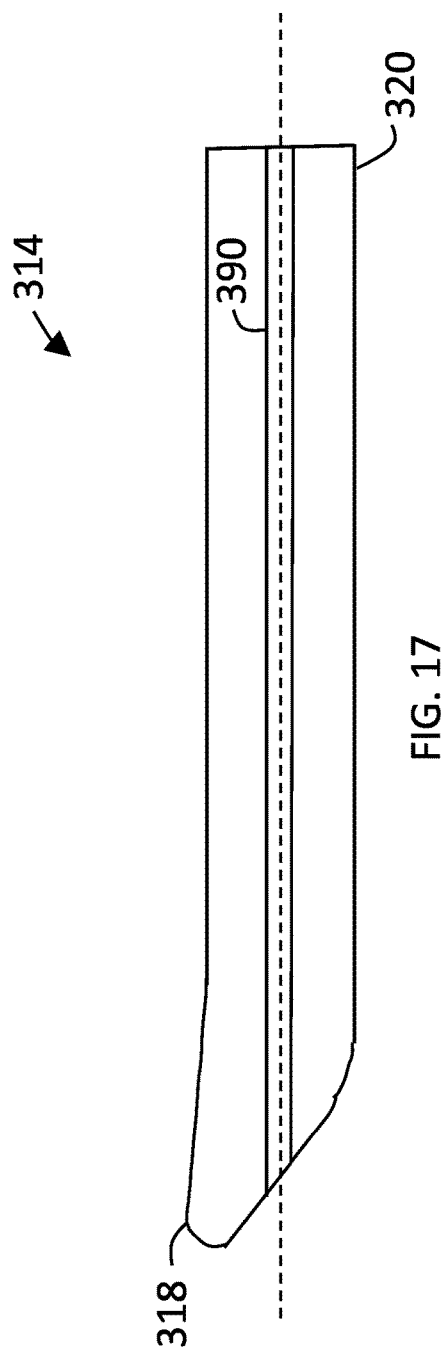
FIG. 17 is a side view of an exemplary tube of a video laryngoscope in accordance with the present disclosure.
Figure 18:
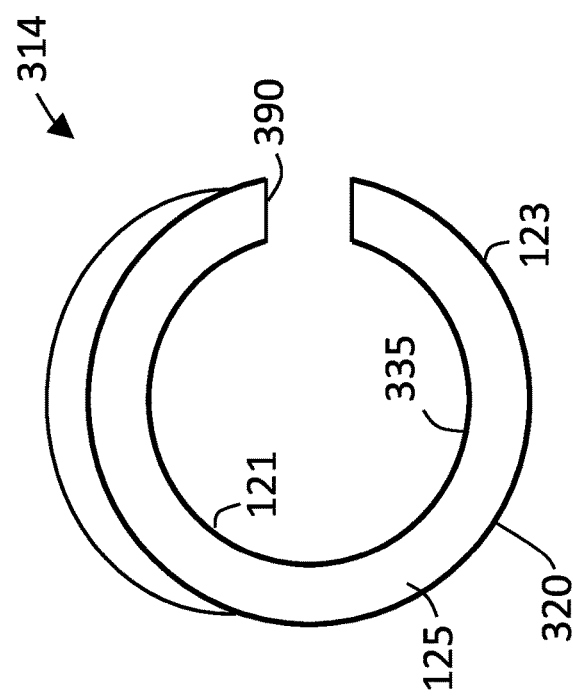
FIG. 18 is a proximal rear view of the exemplary tube of FIG. 17.

In some implementations, as shown in FIGS. 17-18, the tube 314 may a longitudinal slot 390. For example, the tube 314 may have a longitudinal slot 390 extending the length of the tube between the distal end 318 and the proximal end 320. The longitudinal slot 390 may be an open channel. The longitudinal slot 390 may be configured for passage of a breathing tube, suction, jet ventilation, or passage of other instruments into the lumen 129 of the tube 314.

Figure 19:
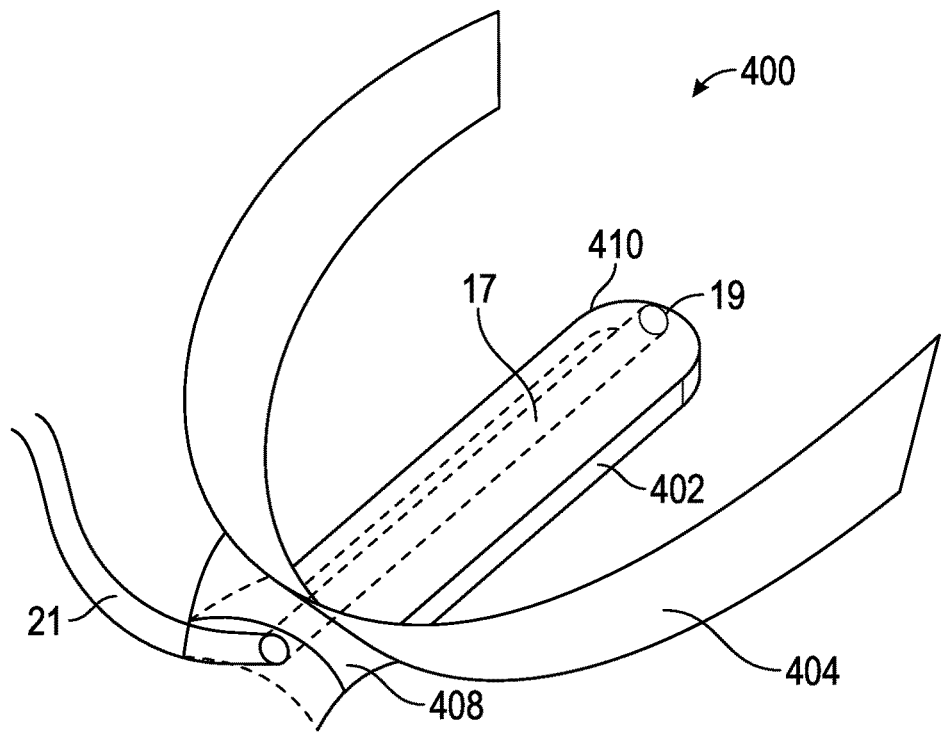
FIG. 19 is a top perspective view of an exemplary camera system attachment device in accordance with the present disclosure.
Figure 20:
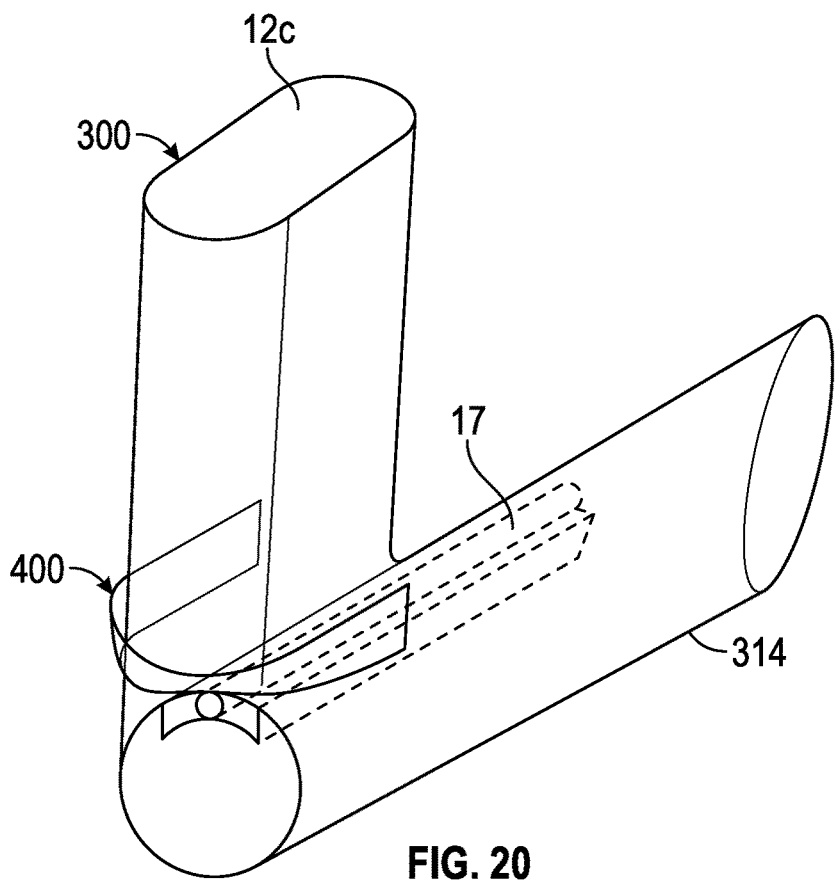
FIG. 20 is a rear perspective view of the camera system attachment device of FIG. 19 in conjunction with an exemplary video laryngoscope in accordance with the present disclosure.
Figure 21:
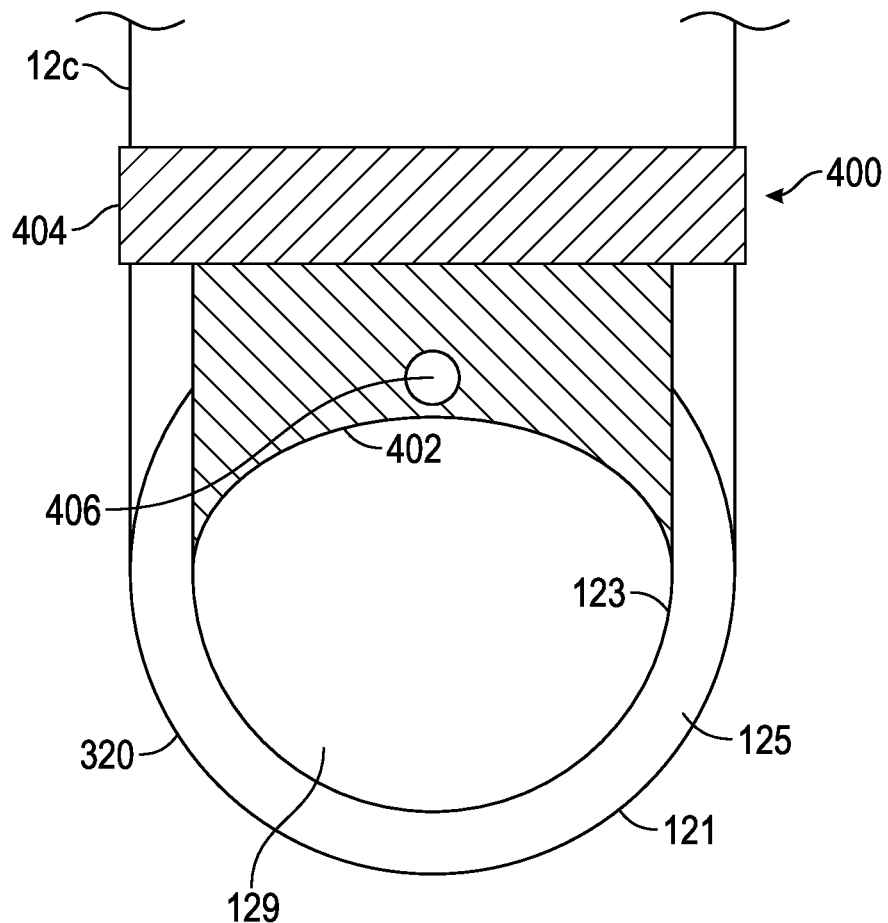
FIG. 21 is a partial front end view of the camera system attachment device in conjunction with an exemplary video laryngoscope of FIG. 20 in accordance with the present disclosure.
Figure 22:
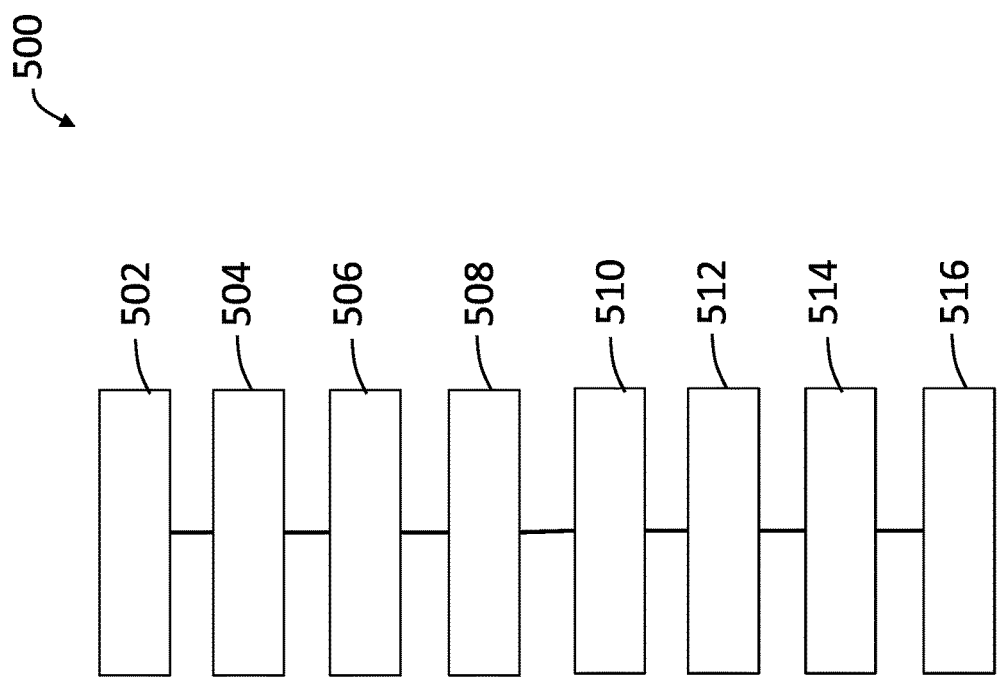
FIG. 22 is a process flow chart of an exemplary method in accordance with the present disclosure.

Turning now to FIGS. 19-21, in some implementations, the camera assembly 17 may be part of a detachable camera system attachment device 400. The camera system attachment device 400 may be used in conjunction with the video laryngoscope 10, 10a, 10b, 100, 300 and/or may be used in conjunction with prior art laryngoscopes, including blades and metal direct laryngoscopes. For illustrative purposes, the camera system attachment device 400 is shown and described in conjunction with the video laryngoscope 300. However, it will be understood that other embodiments or combinations of embodiments may be utilized.

The camera system attachment device 400 may comprise a camera support 402 and a connector 404. The camera support 402 may encompass the camera assembly 17. The camera support 402 may comprise a rigid member having an internal opening 406 configured to encompass all or part of the camera assembly 17. The camera support 402 may protect the camera assembly 17 from contamination. The camera support 402 may have a proximal end 408 and a distal end 410. The camera 19 may be positioned toward the distal end 410 of the camera support 402.

The connector 404 may be connectable to the video laryngoscope 300. The connector 404 may be connectable to the handle 12c of the video laryngoscope 300. In some implementations, the connector 404 may be a clip that is moveable between an open position for attachment to the video laryngoscope 300 and a closed position for securing the camera system attachment device 400 to the video laryngoscope 300. In some implementations, the connector 404 may encompass the majority of the handle 12c and/or may be useable as part of the handle 12c by an operator. In some implementations, the connector 404 may be configured to cover a majority of the handle 12c, such as a soft plastic glove or a snap fit. The connector 404 may conform to the handle 12c and have a similar appearance to the handle. In some implementations, the connector 404 may completely or partially encompass one or more of the other components of the video laryngoscope system 300.

When connected to the video laryngoscope 300 with the connector 404, the camera support 402 may be positioned in the lumen 129 near, or in contact with, the inner surface 123 of the wall 125 of the tube 314. In some implementations, a portion of the camera support 402 may be shaped similarly to a portion of the inner surface 123, so as to fit against the inner surface 123. In some implementations, the camera support 402 may be positioned so as not to interfere with the line of sight of an operator through the lumen 129. In other implementations, the camera support 402 may block portions of the line of sight through the lumen 129.

In some implementations the camera assembly 17 may be wireless, but in implementations where the camera assembly 17 includes the fiber optic cable 21, the fiber optic cable 21 may be positioned from the camera 19 and through the connector 404 to connect to the display(s) 62 and/or computer processor(s) 60. In implementations in which the camera assembly 17 may be wireless, one or more transmission components may be located in the connector 404 and/or the handle 12 and may be configured to transmit signals from the camera assembly 17 to the display(s) 62 and/or computer processor(s) 60.

In use, the distal end 410 of the camera support 402 with the enclosed camera assembly 17 may be inserted through the proximal end 320 of the tube 314, such that the camera 19 is located closer to the proximal end 320 of the tube 314 than the distal end 318 of the tube. The connector 404 may be attached to the handle 12c to secure the camera system attachment device 400 in place. Once the medical procedure is complete, the connector 404 may be detached from the handle 12c and the camera support 402 may be removed from the tube 314. In some implementations, the connector 404 may be removably attached to the camera support 402, such that the connector 404 may be removed and discarded, if, for example, the connector 404 was contaminated during the procedure. In some implementations, all or part of the camera system attachment device 400 may be disposable after one use and/or after contamination.

In use, the video laryngoscope 10, 10a, 10b, 100, 300 may be utilized to view and/or access the airway of a patient such as in an exemplary video laryngoscope method 500, as shown in FIGS. 22-29. For illustrative purposes, the video laryngoscope 300 is shown in the figures. However, it will be understood that other embodiments or combinations of embodiments may be utilized.

A user may hold the video laryngoscope 300 by the handle 12c. In implementations in which the handle 12c is hingedly connected to the tube 314, the user may move the handle 12c from a first position to a second position. In some implementations, the light source 135 may be activated automatically when the user moves the handle 12c from the first position to the second position. In some implementations, the user may activate the light source 135, such that the light source 135 emits light through and/or from the tube 314. In some implementations, the light source 135 may be activated automatically when the user removes the video laryngoscope 300 from packaging.

Figure 23:
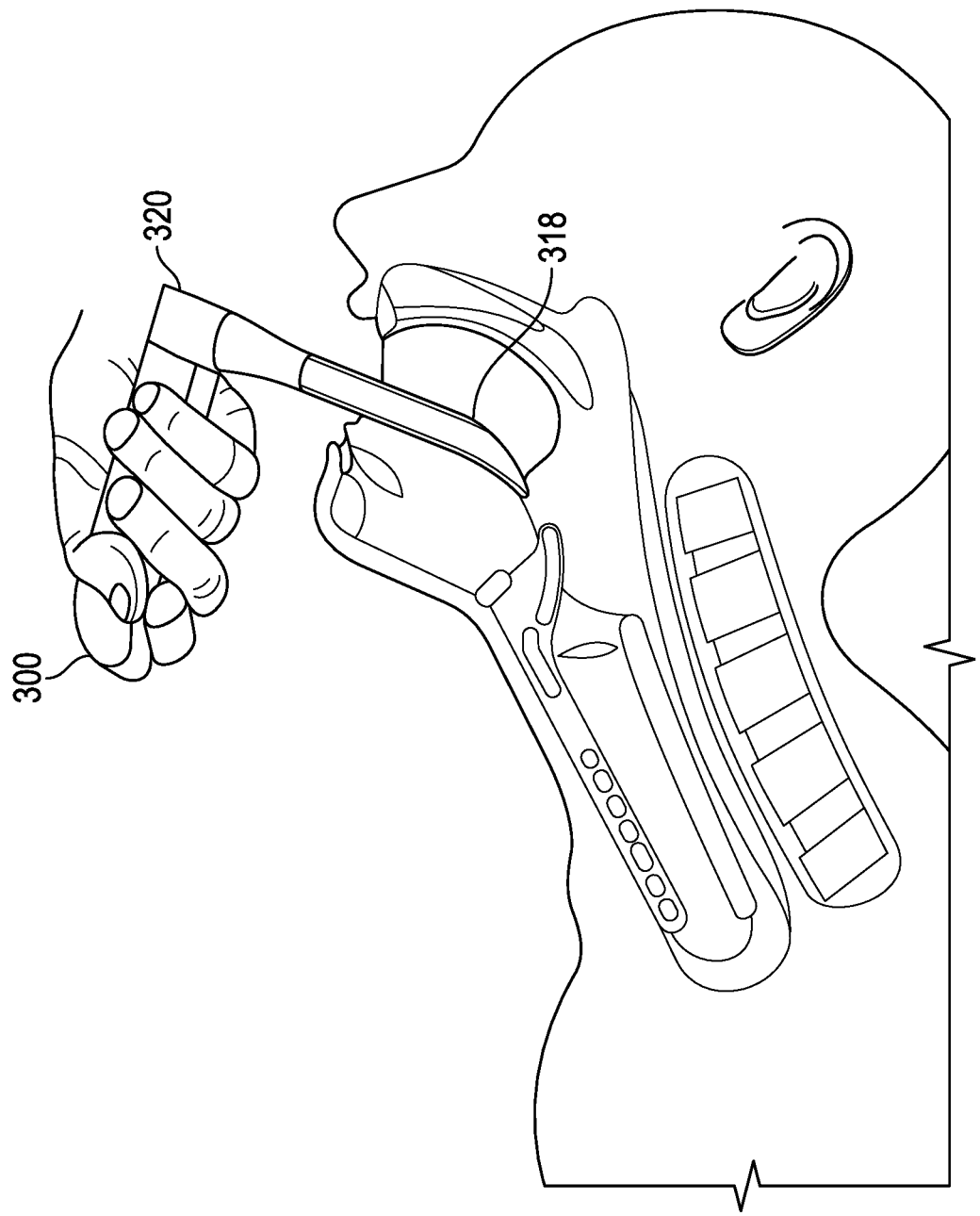
FIG. 23 is an illustration of an exemplary use of a video laryngoscope in accordance with the present disclosure.
Figure 24A:
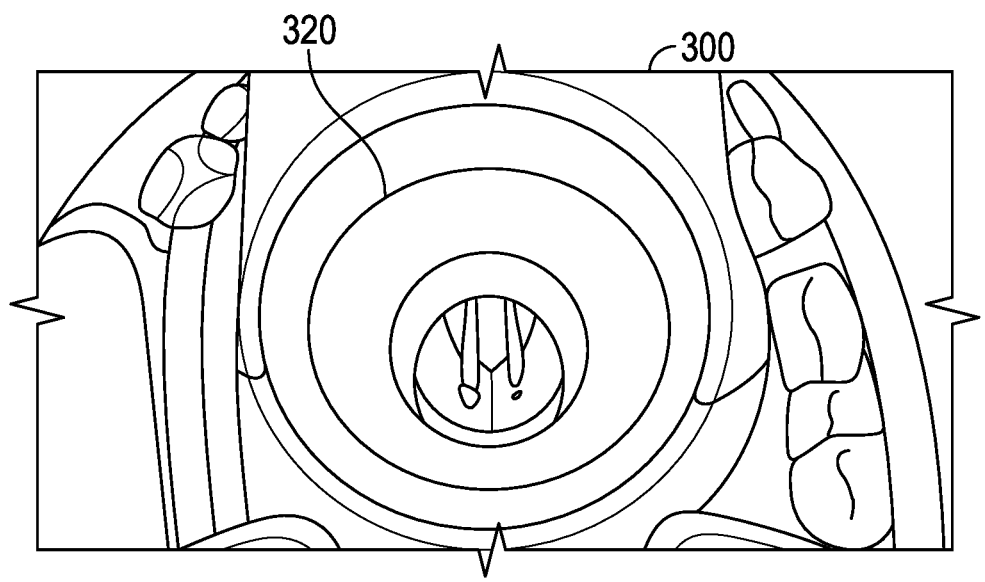
FIG. 24A is an illustration of an exemplary use of a video laryngoscope in accordance with the present disclosure.
Figure 24B:
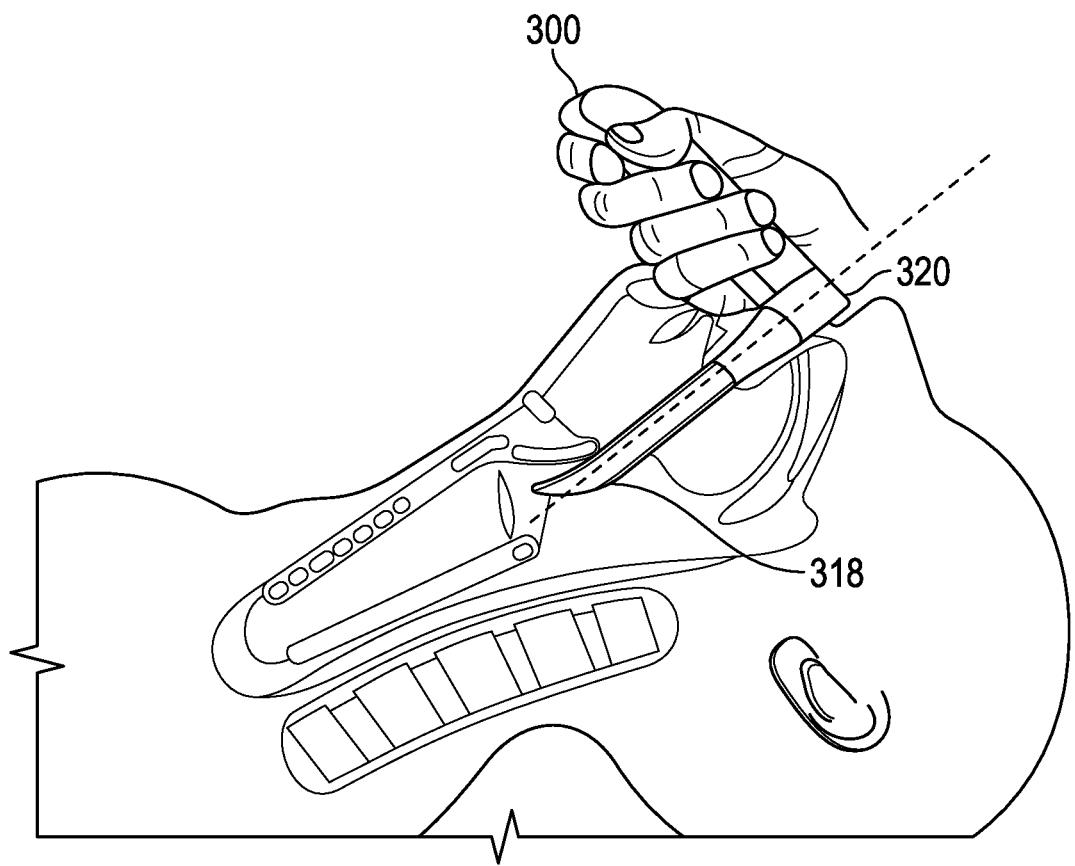
FIG. 24B is an illustration of an exemplary use of a video laryngoscope in accordance with the present disclosure.
Figure 25:
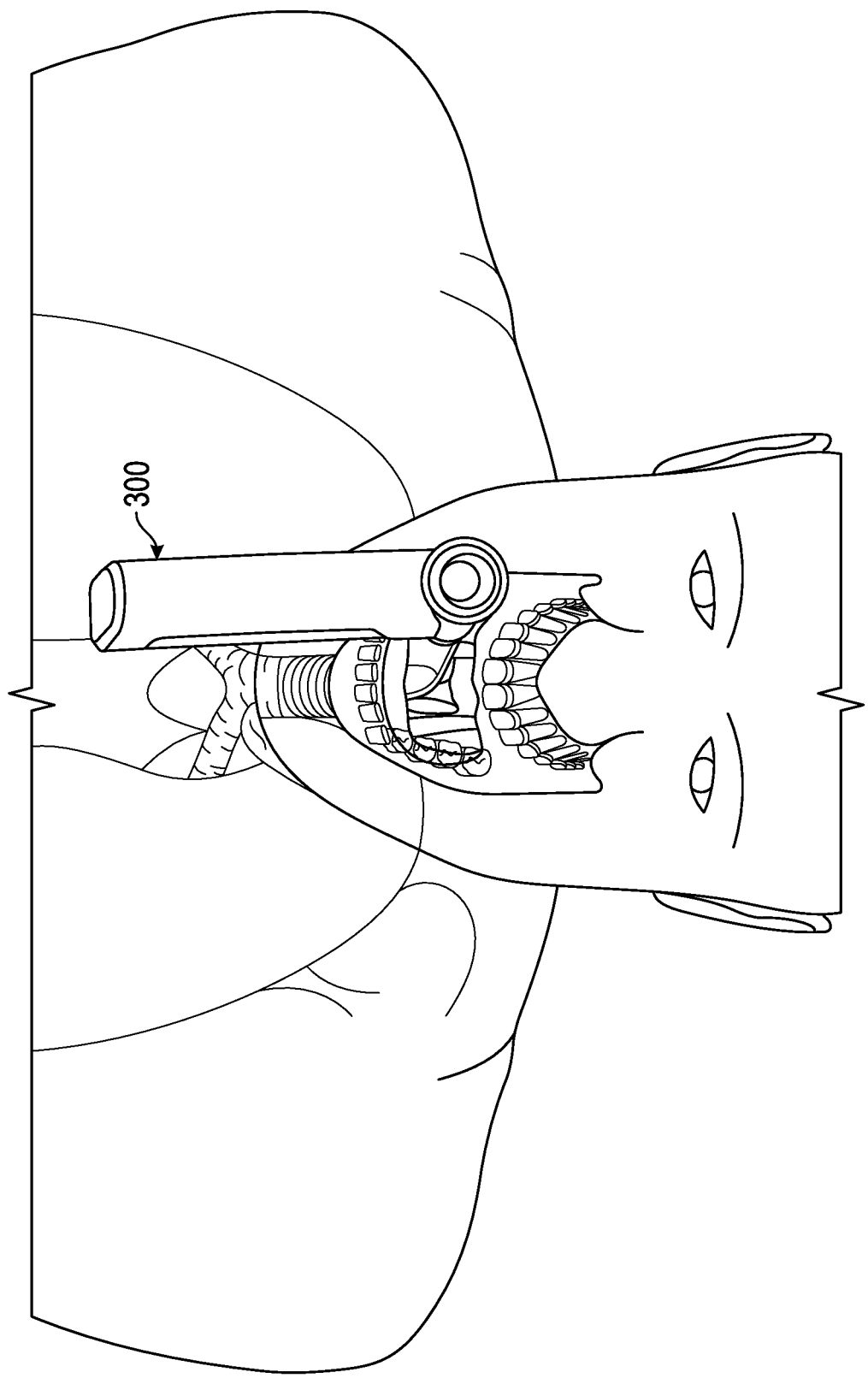
FIG. 25 is an illustration of an exemplary use of a video laryngoscope in accordance with the present disclosure.
Figure 26A:
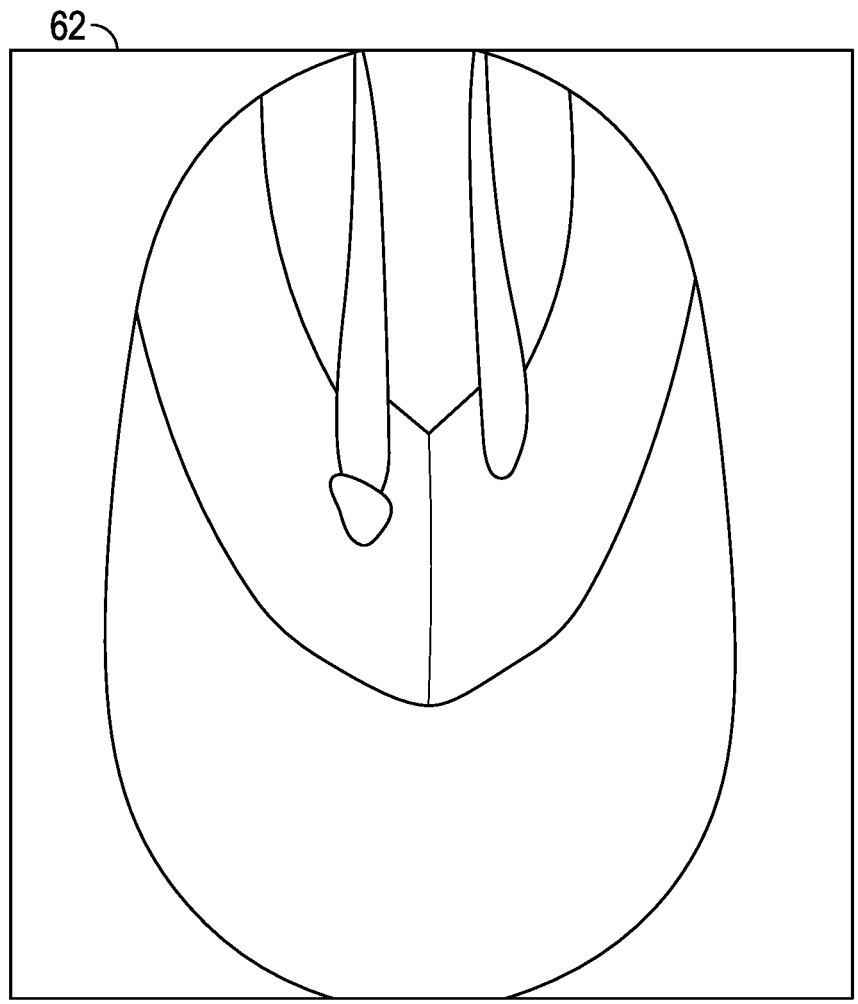
FIG. 26A is an illustration of an exemplary display screen in use in accordance with the present disclosure.
Figure 26B:
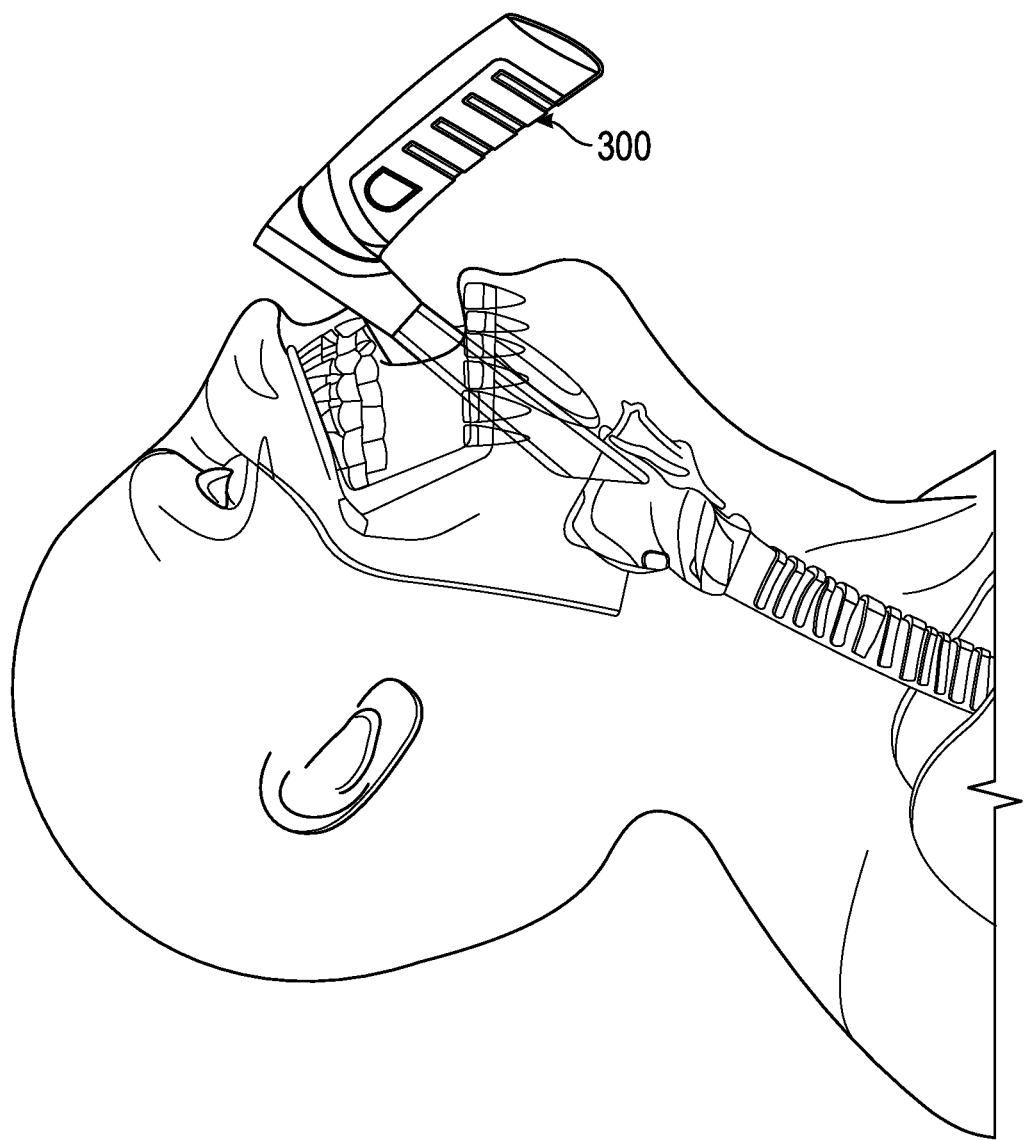
FIG. 26B is an illustration of an exemplary use of a video laryngoscope in accordance with the present disclosure.

In step 502, as shown in FIG. 23, the user may insert the tube 314 into the mouth of the patient, starting with the distal end 318 of the tube 314. Once the video laryngoscope 300 is inserted, the user has a direct line of sight to the larynx of the patient through the cylindrical tube 314, as shown in FIGS. 24A, 24B, and 25.

As illustrated in FIGS. 26A, 26B, 27A, and 27B, in step 504, the camera assembly 17 may capture one or more images, which may be in the form of a video, similar to the viewpoint of the user through the lumen 129, as the camera 19 may have a field of view at least partially outside of the distal end 318 of the tube 314. In step 506, the camera assembly 17 may transfer the images, wirelessly and/or via a physical connection, to the one or more computer processor 60 and/or the one or more display screens 62. The displayed images may be larger than the actual structure of the patient, or may be magnified to be larger. In step 508, the operator may use the images on the display screen 62, and/or the direct line of sight through the lumen 129, to position the distal end 318 of the tube 314 under the epiglottis and to the vocal cords of the patient. The central longitudinal axis L1 of the tube 314 may extend between the vocal cords when the video laryngoscope 300 is in position. In some implementations, the distal end 318 of the tube 314 may be positioned between the vocal cords. In some implementations, the operator may use the handle 12c to rotate the tube 314 within the throat of the patient to align the central longitudinal axis of the lumen 129 to extend between the vocal cords. In some implementations, the operator may use the tube 314 to displace tissues within the throat to maneuver the tube 314 to create a line of sight to the vocal cords through the lumen 129.

In some implementations, the images may be duplicated onto two or more display screens 62. In some implementations, a downloadable software application on a user device, such as a smart phone, may be used to receive and display the images, and/or to mirror the images onto another display screen 62. HIPPA compliance may be required and/or confirmed to access the images. In some implementations, the images may be stored. In some implementations, software may be configured to record information into one or more databases, such as HIPPA compliant databases. The information may include the images and/or specific information about the patient or use of the video laryngoscope 300.

The operator may use the display screen(s) 62 and may additionally (or alternatively) use the direct line of sight through the tube 314 to the vocal cords. The ability to use either or both of the display screen 62 and a manual line of sight allows the operator to inspect the throat and position the tube 314 under many different conditions.

Figure 27A:
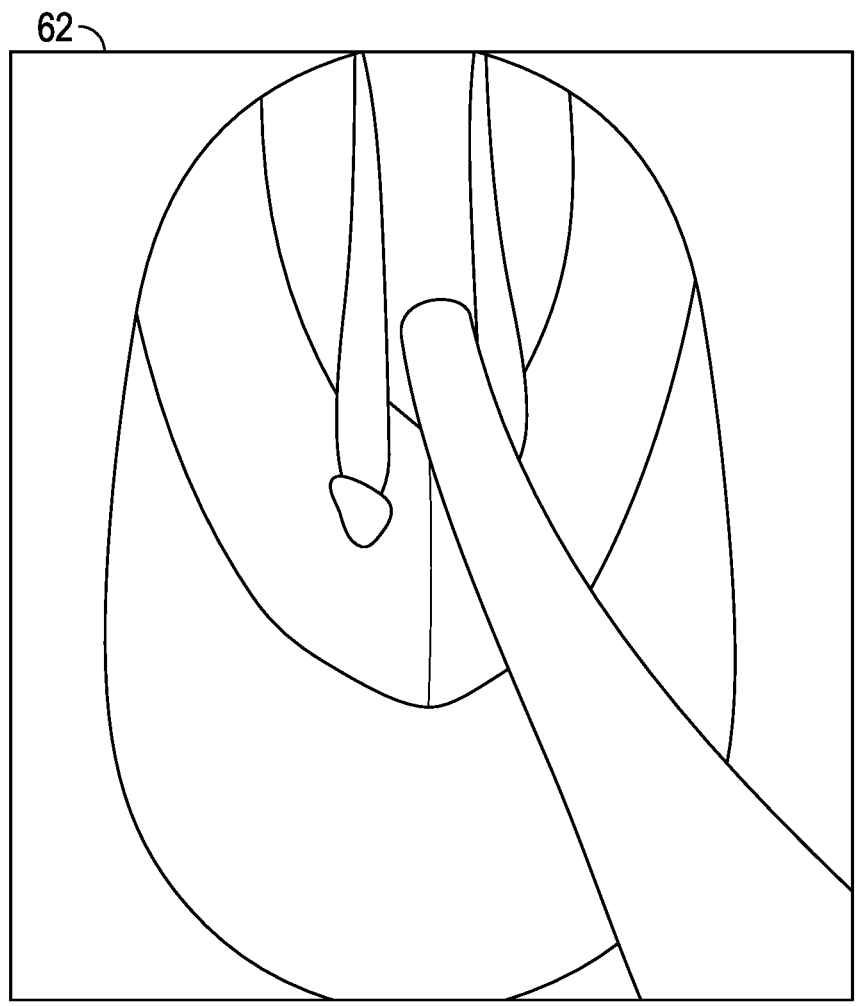
FIG. 27A is an illustration of an exemplary display screen in use in accordance with the present disclosure.
Figure 27B:
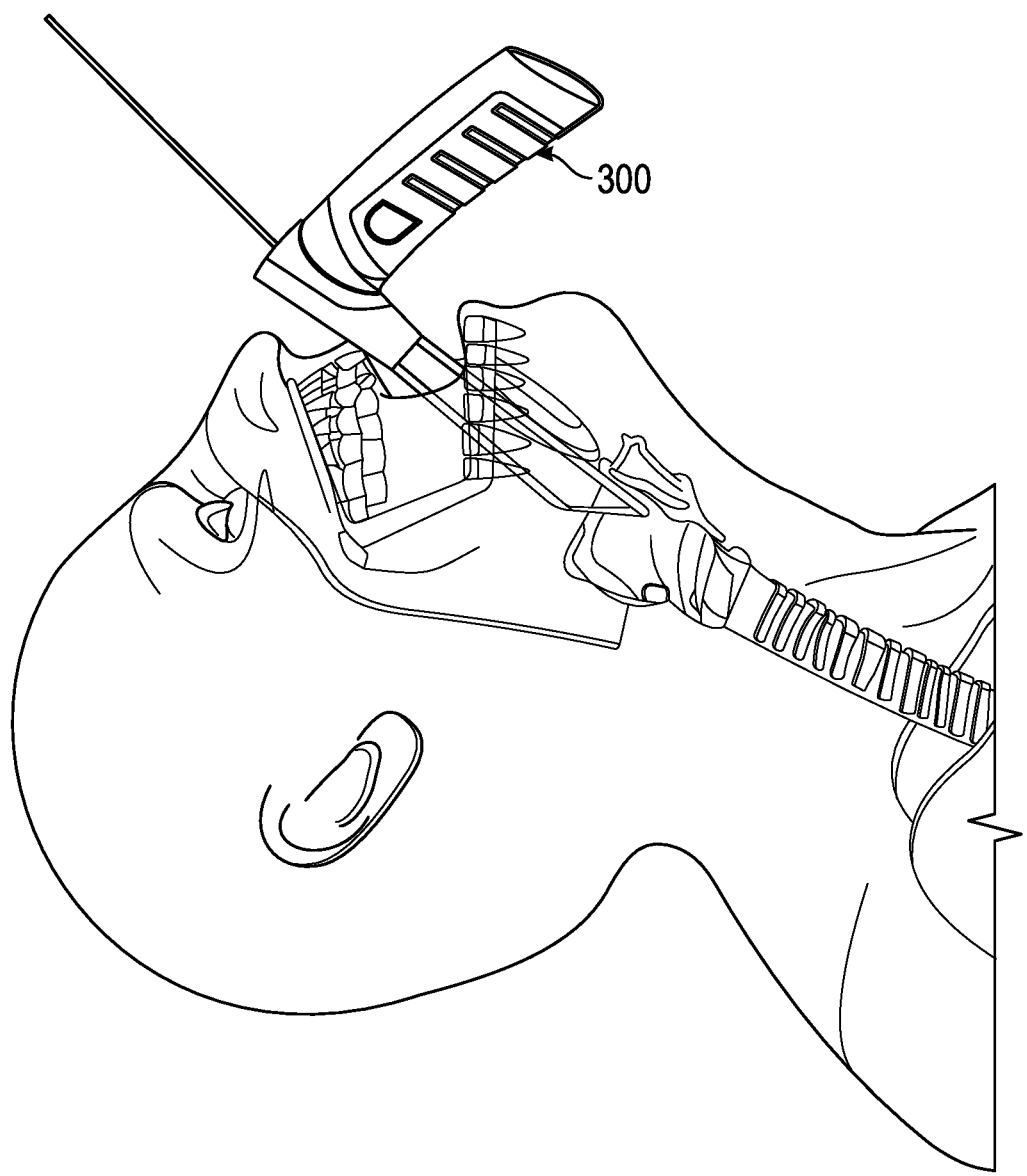
FIG. 27B is an illustration of an exemplary use of a video laryngoscope in accordance with the present disclosure.
Figure 28:
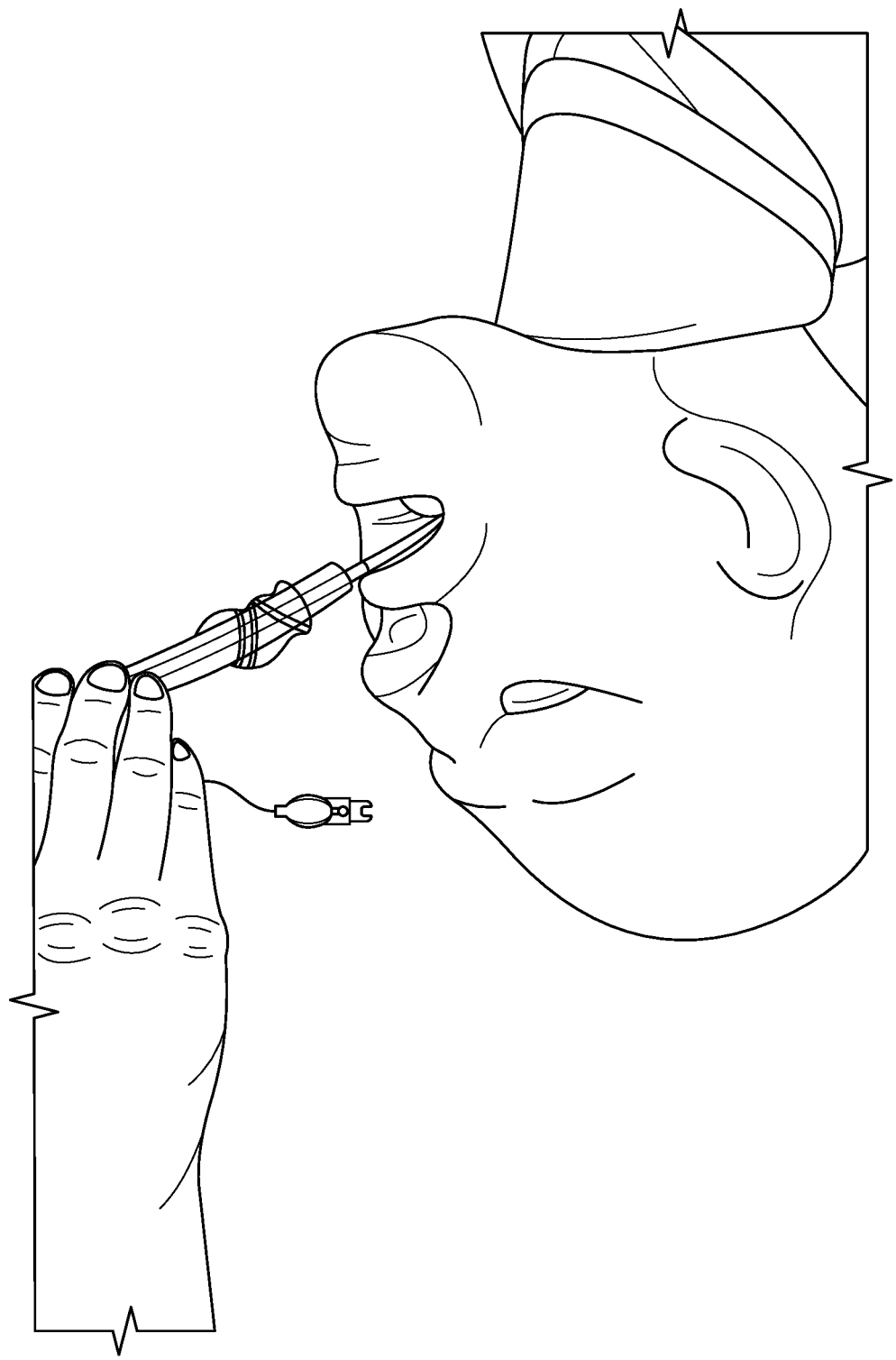
FIG. 28 is an illustration of a portion of a method of use of a video laryngoscope in accordance with the present disclosure.
Figure 29:
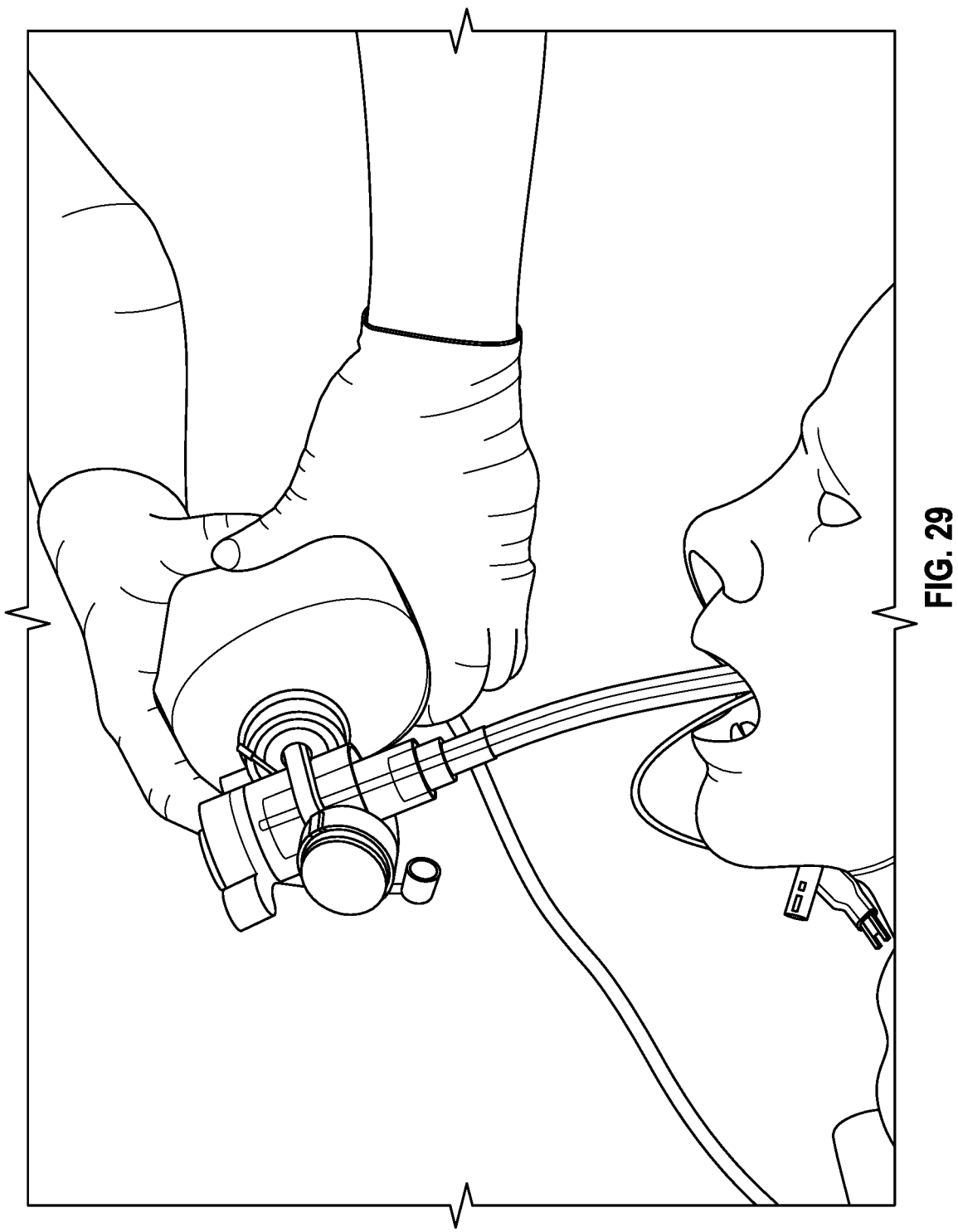
FIG. 29 is an illustration of a portion of a method of use of a video laryngoscope in accordance with the present disclosure.

In some implementations, in step 510, after the tube 314 is inserted, a bougie (or other devices, such as a suction tube) may be inserted through the cylindrical tube 314 between the vocal cords of the patient and into the trachea of the patient, as shown in FIGS. 27A and 27B. In step 512, the video laryngoscope 300 may be removed along the bougie, leaving the bougie in place. In step 514, the bougie may then be used to guide an endotracheal tube into the trachea, as shown in FIG. 28. Once in place, in step 516, the bougie is then removed and the endotracheal tube can be used to ventilate the patient, as shown in FIG. 29.

In some implementations, the video laryngoscope 300 may be disposable (or single use), allowing its inclusion with a bougie and/or suction catheter into an emergency airway kit to be used by emergency medical services inside, as well as outside of, a medical (hospital) facility. Furthermore, the video laryngoscope 300 may be partially disposable. For example, the handle 12c and the camera assembly 17 may be reused, while the cylindrical tube 314 may be discarded. In such a situation, parts of the video laryngoscope 300 that actually was inserted in a patient may be disposed of while the remaining portions may be reused, creating a savings on cleaning and replacement costs. In some implementations, the video laryngoscope 300 is at least partially reusable. The position of the camera assembly 17 toward the proximal end of the tube 314 may avoid soiling of the camera 19 by secretions and blood.

In some implementations, the video laryngoscope 10, 10a, 10b, 100, 300 may be used for training operators to insert bougies and intubation tubes into the throat. In some implementations, the display screen 62 may be used to train operators what features to look for within the throat for physical examinations and/or correct insertions of bougies and intubation tubes into the throat.

CONCLUSION

Conventionally, typical laryngoscopes do not have video capability, do not combine video capability with direct manual visibility, and/or are too bulky for ease of use and transport. The present disclosure addresses these deficiencies with a video laryngoscopes and methods of use. In accordance with the present disclosure, a video laryngoscope may comprise a camera assembly positioned at least partially within a tube and having a field of view through a distal end opening of the tube, such as of the interior of the throat of a patient, which may be used for visualizing the vocal chords of a patient to position an endotracheal tube for intubation and ventilation of the patient, for example.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Elements and features of one embodiment may be used in combination with, or replacing, elements and features of other embodiments. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment.

What is claimed is:

1. A laryngoscope, comprising:
   a handle having a proximal end and a distal end;
   a tube having a proximal end, a distal end, a length extending between the proximal end and the distal end, and a first longitudinal axis along the length of the tube, the proximal end connected to the proximal end of the handle, the tube having an inner surface defining a lumen internal space along the length of the tube, the lumen internal space creating a direct line of sight along the first longitudinal axis through the tube; and
   a camera positioned on one of the inner surface and the outer surface of the tube to have a field of view beyond the distal end of the tube, the camera having a second longitudinal axis offset from the first longitudinal axis of the tube such that the direct line of sight along the first longitudinal axis through the tube is unobstructed.

2. The laryngoscope of claim 1, further comprising a light source injecting light into the tube, wherein the light source is a circular light source.

3. The laryngoscope of claim 1, further comprising a light source injecting light into the tube, wherein the light source comprises a ring of one or more light emitting diodes.

4. The laryngoscope of claim 1, wherein the lumen internal space has a first diameter, and the camera has a second diameter that is less than approximately 10% of the first diameter.

5. The laryngoscope of claim 1, wherein the camera is one of a fiber optic camera and a chip-on-tip camera.

6. The laryngoscope of claim 1, wherein the second longitudinal axis of the camera is parallel to and laterally offset from the first longitudinal axis of the lumen internal space.

7. The laryngoscope of claim 1, further comprising:
   one or more computer processors in communication with the camera; and
   one or more display screens in communication with the one or more computer processors such that images captured by the camera are displayable on the one or more display screens.

8. The laryngoscope of claim 7, wherein a first display screen of the one or more display screens is separate from the tube and the handle.

9. The laryngoscope of claim 7, wherein the one or more display screens include a first display screen and a second display screen configured to display the images.

10. A method of use of a laryngoscope, comprising:
    inserting a tube of a laryngoscope into a mouth of a patient, the tube having a proximal end, a distal end, a length extending between the proximal end and the distal end, and a central longitudinal axis along the length of the tube, the tube having an inner surface defining a lumen internal space along the length of the tube, the lumen internal space creating a direct line of sight along a longitudinal axis through the tube, the proximal end of the tube connected to a proximal end of a handle; and
    obtaining video images from a camera positioned on one of the inner surface and the outer surface of the tube and having a field of view out of the distal end of the tube, the camera having a longitudinal axis offset from the longitudinal axis of the tube such that the direct line of sight along the longitudinal axis through the tube is unobstructed.

11. The method of claim 10, further comprising viewing at least a portion of the patient through the tube when video images are being obtained.

12. A laryngoscope, comprising:
    a handle having a proximal end and a distal end;
    a tube having a proximal end, a distal end, a length extending between the proximal end and the distal end, and a first longitudinal axis along the length of the tube, the proximal end connected to the proximal end of the handle, the tube having an inner surface defining a lumen internal space along the length of the tube and an outer surface, the lumen internal space creating a direct line of sight along the first longitudinal axis through the tube; and
    a camera positioned on one of the inner surface and the outer surface of the tube to have a field of view beyond the distal end of the tube, the camera having a second longitudinal axis offset from the first longitudinal axis of the tube such that the direct line of sight along the first longitudinal axis through the tube is unobstructed.

13. A camera system attachment device for attachment to a laryngoscope, comprising:

a camera support having a rigid member with a longitudinal axis and an opening along the longitudinal axis, the camera support having a proximal end and a distal end, the camera support configured to be positioned within a lumen of a laryngoscope such that a direct line of sight through the lumen of the laryngoscope is unobstructed;

a camera assembly positioned within the opening, the camera assembly comprising a camera positioned toward the distal end of the camera support; and a connector attached to the camera support and connectable to a handle of the laryngoscope to secure the camera support in the lumen of the laryngoscope.

14. The camera system attachment device of claim 13, wherein the connector is removably attached to the camera support.

\* \* \* \* \*